(12) United States Patent
Matsuo et al.

(10) Patent No.: US 12,139,449 B2
(45) Date of Patent: Nov. 12, 2024

(54) METHOD AND CATALYST FOR PRODUCING ALCOHOL

(71) Applicant: Mitsubishi Chemical Corporation, Tokyo (JP)

(72) Inventors: Takeshi Matsuo, Tokyo (JP); Yumiko Yoshikawa, Tokyo (JP); Naoyuki Sakamoto, Tokyo (JP); Takayuki Aoshima, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 726 days.

(21) Appl. No.: 17/154,118

(22) Filed: Jan. 21, 2021

(65) Prior Publication Data

US 2021/0139398 A1 May 13, 2021

Related U.S. Application Data

(63) Continuation of application No. PCT/JP2019/028633, filed on Jul. 22, 2019.

(30) Foreign Application Priority Data

Jul. 23, 2018 (JP) ................. 2018-137792

(51) Int. Cl.
    *C07C 29/136* (2006.01)
    *B01J 23/14* (2006.01)
    *B01J 23/36* (2006.01)
    *C01G 25/02* (2006.01)

(52) U.S. Cl.
    CPC ............ *C07C 29/136* (2013.01); *B01J 23/14* (2013.01); *B01J 23/36* (2013.01); *C01G 25/02* (2013.01); *C01P 2006/12* (2013.01)

(58) Field of Classification Search
    CPC ......... C07C 29/136; B01J 23/16; B01J 29/89; B01J 23/36
    See application file for complete search history.

(56) References Cited

U.S. PATENT DOCUMENTS

| | | | |
|---|---|---|---|
| 4,317,918 A * | 3/1982 | Takano | C07C 29/149 568/861 |
| 4,782,167 A | 11/1988 | Rao | |
| 6,376,414 B1 | 4/2002 | Antons et al. | |
| 6,765,118 B2 | 7/2004 | Fischer et al. | |
| 7,378,365 B2 | 5/2008 | Boldingh et al. | |
| 7,423,190 B2 | 9/2008 | Boldingh et al. | |
| 8,692,025 B2 | 4/2014 | Lanver et al. | |
| 2003/0050516 A1 | 3/2003 | Fischer et al. | |
| 2006/0030743 A1 * | 2/2006 | Schubert | C07B 41/02 568/880 |
| 2006/0116521 A1 | 6/2006 | Fischer et al. | |
| 2008/0026931 A1 | 1/2008 | Boldingh et al. | |
| 2008/0027258 A1 | 1/2008 | Boldingh et al. | |
| 2008/0216391 A1 * | 9/2008 | Cortright | C10L 1/1857 44/307 |
| 2010/0197485 A1 | 8/2010 | Johnston et al. | |
| 2011/0105313 A1 | 5/2011 | Oudart et al. | |
| 2012/0209030 A1 | 8/2012 | Lanver et al. | |
| 2014/0121400 A1 | 5/2014 | Liu et al. | |

FOREIGN PATENT DOCUMENTS

| | | |
|---|---|---|
| EP | 3 594 195 A1 | 1/2020 |
| JP | 63-21 8636 A | 9/1988 |
| JP | 63-301845 A | 12/1988 |
| JP | 04-099753 A | 3/1992 |
| JP | 06-116182 A | 4/1994 |
| JP | 06-179667 A | 6/1994 |
| JP | 07-118187 A | 5/1995 |
| JP | 08-245444 A | 9/1996 |
| JP | 11-199530 A | 7/1999 |
| JP | 2000-007596 A | 1/2000 |
| JP | 2000-342968 A | 12/2000 |
| JP | 2001-046873 A | 2/2001 |
| JP | 2001-046874 A | 2/2001 |
| JP | 2001-157841 A | 6/2001 |
| JP | 2002-501817 A | 1/2002 |
| JP | 2003-528064 A | 9/2003 |
| JP | 2005-537327 A | 12/2005 |
| JP | 2006-505399 A | 2/2006 |
| JP | 2008-055413 A | 3/2008 |
| JP | 2013-508326 A | 3/2013 |
| JP | 2013-508362 A | 3/2013 |

(Continued)

OTHER PUBLICATIONS

International Search Report issued Oct. 15, 2019 in PCT/JP2019/028633 filed on Jul. 22, 2019, 3 pages.

Ly et al., "Effect of Addition Mode of Re in Bimetallic Pd—Re/$TiO_2$ Catalysts Upon the Selective Aqueous-Phase Hydrogenation of Succinic Acid to 1,4-Butanediol", Topics in Catalysis 55, 2012, pp. 466-473.

Broadbent et al., "Rhenium and Its Compounds as Hydrogenation Catalysts. III. Rhenium Heptoxide", Journal of Organic Chemistry 24, 1959, pp. 1847-1854.

Rozmys Ł owicz et al., "Selective Hydrogenation of fatty acids to alcohols over highly dispersed $ReO_x/TiO_2$ catalyst", Journal of Catalysis 328, 2015, pp. 197-207.

(Continued)

*Primary Examiner* — Yate' K Cutliff
(74) *Attorney, Agent, or Firm* — Oblon, McClelland, Maier & Neustadt, L.L.P.

(57) ABSTRACT

An alcohol production method in which an alcohol is produced from a carbonyl compound, the method including producing an alcohol by using a catalyst, the catalyst including a metal component including rhenium having an average valence of 4 or less and a carrier supporting the metal component, the carrier including zirconium oxide. A catalyst for producing an alcohol by hydrogenation of a carbonyl compound, the catalyst including a carrier including zirconium oxide and a metal component supported on the carrier, the metal component including rhenium having an average valence of 4 or less.

18 Claims, No Drawings

(56) References Cited

FOREIGN PATENT DOCUMENTS

| JP | 2015-048349 A | 3/2015 |
|---|---|---|
| JP | 2015-074619 A | 4/2015 |
| JP | 2016-500697 A | 1/2016 |

OTHER PUBLICATIONS

Toyao et al., "$TiO_2$-Supported Re as a General and Chemoselective Heterogeneous Catalyst for Hydrogenation of Carboxylic Acids to Alcohols" Chemistry A European Journal 23, 2017, pp. 1001-1006.
Takeda et al., "Characterization of Re—Pd/$SiO_2$ Catalysts for Hydrogenation of Stearic Acid", ACS Catalysis 5, 2015, pp. 7034-7047.
Combined Chinese Office Action and Search Report issued Oct. 26, 2022 in Patent Application No. 201980049291.4 (with English machine translation and English translation of Category of Cited Documents), 18 pages.
Japanese Office Action issued on Jan. 24, 2023 in Japanese Patent Application No. 2020-532378 (with English translation), 11 pages.
Extended European Search Report issued Jul. 16, 2021 in European Patent Application No. 19840190.3, 7 pages.

\* cited by examiner

METHOD AND CATALYST FOR PRODUCING ALCOHOL

TECHNICAL FIELD

The present invention relates to a method for producing an alcohol by hydrogenation of a carbonyl compound. The present invention also relates to a catalyst suitable as a catalyst for hydrogenation of a carbonyl compound, that is, a catalyst for producing an alcohol by hydrogenation of a carbonyl compound, and a method for producing such a catalyst.

BACKGROUND ART

Methods in which a carbonyl compound is hydrogenated to form a corresponding alcohol have long been known. For example, a common method for producing an alcohol from an organic carboxylic acid is to esterify a carboxylic acid with a lower alcohol and subsequently perform reduction using an Adkins catalyst (copper chromium catalyst).

However, the production of an alcohol with a copper catalyst, which is commonly conducted under a severe condition such as a hydrogen pressure of 200 atmospheres or more, is an uneconomical process that consumes a large amount of energy for producing an alcohol with various facility restrictions.

Furthermore, since a copper catalyst is not capable of directly reducing an organic carboxylic acid, a carboxylic acid needs to be converted into a carboxylic acid ester before a reduction treatment is performed. Therefore, a multistage reaction process needs to be conducted in order to produce an intended alcohol. This increases the complexity of the process.

Moreover, in the case where a two-stage alcohol production method is used, for example, it becomes considerably difficult to selectively produce a hydroxycarboxylic acid using a polyvalent carboxylic acid as a raw material by converting some of the carboxylic acid functional groups into alcohol functional groups.

In contrast, a method in which a carboxylic acid is directly hydrogenated (reduced) in one stage to produce a corresponding alcohol with high selectivity is an economically advantageous process. Even in the case where a polyvalent carboxylic acid is used as a raw material, it is possible to selectively produce a corresponding hydroxycarboxylic acid by appropriately controlling the reaction conditions.

For use in such a process, there have been proposed various metal-supported catalysts that include a noble metal belonging to Groups 8 to 10 of the periodic table as a catalytic activity component.

For example, there have been proposed a catalyst produced by supporting palladium and rhenium on a carrier and subsequently performing a reduction treatment with hydrogen or the like (e.g., PTL 1 and NPL 1) and a catalyst produced by supporting ruthenium and tin on a carrier and subsequently performing a reduction treatment with hydrogen or the like (e.g., PTLs 2 and 3).

The above catalysts are suitable catalysts that produce a high reaction activity and high reaction selectivity in the reduction of a carboxylic acid and/or a carboxylic acid ester. There has also been proposed a hydrogenation reaction of a particular carboxylic acid in which a cobalt catalyst that includes lanthanum and palladium, which is an example of the above-described catalysts, is used (e.g., PTL 4).

On the other hand, there have also been proposed catalysts that do not include any of the expensive noble metals of Groups 8 to 10 of the periodic table. For example, a catalyst including rhenium that serves as a catalytic component has been reported since a long time ago (e.g., NPL 2). There has also been proposed a tin-containing rhenium catalyst for use in a hydrogenation reaction of a particular carboxylic acid (e.g., PTL 5).

Recently, there has been reported a method for selectively producing an intended alcohol under further mild conditions. In the production method, a metal-supported catalyst including rhenium that serves as a catalytic activity component is used (e.g., NPLs 3 and 4). It has been reported that, as described in Supporting Information of NPL 4, titanium oxide is specifically effective as a carrier for the catalyst including rhenium serving as a catalytic activity component because such a carrier produces a significant catalytic activity.

However, since catalysts including rhenium that serves as a catalytic activity component have a lower catalytic activity than catalysts including a noble metal, it is common to use, as a supported metal, rhenium in combination with a noble metal belonging to Groups 8 to 10 of the periodic table or to use cobalt, which belongs to Group 9 of the periodic table, as a carrier (e.g., PTLs 6, 7, 8, and 9 and NPL 5).

PTL 1: JPS 63-218636A
PTL 2: JP 2000-007596A
PTL 3: JP 2001-157841A
PTL 4: JPS 63-301845A
PTL 5: JPH 4-99753A
PTL 6: JPH 6-116182A
PTL 7: JP 2002-501817A
PTL 8: JP 2016-500697A
PTL 9: JPH 7-118187A
NPL 1: Topics in Catalysis 55 (2012) 466-473
NPL 2: Journal of Organic Chemistry 24 (1959) 1847-1854
NPL 3: Journal of Catalysis 328 (2015) 197-207
NPL 4: Chemistry A European Journal 23 (2017) 1001-1006
NPL 5: ACS Catalysis 5 (2015) 7034-7047

Among the hydrogenation catalysts known in the related art, a catalyst including a noble metal belonging to Groups 8 to 10 of the periodic table which serves as a catalytic activity component, which is produced using an expensive noble metal, increases the costs of production of a catalyst. In addition, such a catalyst is typically likely to cause side reactions and reduce reaction selectivity. Examples of the side reactions include a reaction that reduces the number of carbons of the resulting alcohol due to decarboxylation, a defunctionalization reaction associated with dehydration and hydrogenation of the reaction product, and an esterification reaction of the carboxylic acid used as a raw material with the alcohol produced.

For example, as for a palladium metal-supported catalyst containing rhenium, the addition of rhenium increases the rate of catalytic reaction in which succinic acid is converted into the hydride of succinic acid, that is, butanediol, as described in NPL 1. However, the above-described side reactions also occur simultaneously, which reduce the productivity of the reaction product and increase the purification costs. In addition, the catalytic activity is still at an insufficient level.

As for the catalysts that include a catalytic component, such as tin, in addition to a noble metal belonging to Groups 8 to 10 of the periodic table as proposed in PTLs 2 and 3, the addition of tin or the like increases reaction selectivity. However, the addition of such catalytic components may disadvantageously reduce catalytic activity. This results in a necessity to further use a large amount of expensive noble metal, such as platinum, and increases the costs of production of a catalyst.

A catalyst that includes rhenium serving as a catalytic activity principal component and titanium oxide serving as a carrier may lead to the establishment of a process that is markedly economical in that the catalyst does not contain any expensive noble metals.

However, the rhenium-supporting titanium oxide catalysts known in the related art are hard-to-handle catalysts that become deactivated significantly upon being brought into contact with an oxidizing gas, such as air or oxygen.

Specifically, the known catalysts that include rhenium serving as a catalytic activity component have the issues described below:

1) In an industrial process, the catalysts are likely to become deactivated during charging or regeneration of the catalysts. This increases the complexity of handling of the catalysts. A catalyst that includes a deactivated catalytic component has a lower activity than catalysts that include a noble metal. This reduces productivity.

2) A high Lewis acidity of high-valent rhenium species may facilitate an esterification reaction of the carboxylic acid used as a raw material with the alcohol produced.

3) Particularly as the reaction conversion increases, a defunctionalization reaction may significantly occur due to the dehydration and hydrogenation of the alcohol produced. This may significantly reduce the selectivity of the alcohol that is to be produced.

SUMMARY OF INVENTION

An object of the present invention is to provide a high-activity rhenium-supporting catalyst that is a metal-supported catalyst that includes rhenium serving as a catalytic activity component, the catalyst having the features described below, a method for producing the catalyst, and a method for producing an alcohol with the catalyst.

i) the catalyst is capable of producing an intended alcohol at a high yield with high selectivity by the hydrogenation reaction of a carbonyl compound, while reducing the above-described various side reactions to a sufficient degree.

ii) the catalyst can be handled in air, making it easier to handle, and economical.

The inventors of the present invention found that the above-described issues may be addressed by a specific catalyst that includes a zirconium oxide carrier and rhenium supported on the carrier and made the present invention.

The summary of the present invention is as follows.

[1] An alcohol production method in which an alcohol is produced from a carbonyl compound, the method comprising producing an alcohol by using a catalyst, the catalyst including a metal component including rhenium having an average valence of 4 or less and a carrier supporting the metal component, the carrier including zirconium oxide.

[2] The alcohol production method according to [1], wherein the carrier includes at least monoclinic and/or tetragonal zirconium oxide.

[3] The alcohol production method according to [2], wherein the carrier includes at least monoclinic zirconium oxide.

[4] The alcohol production method according to [3], wherein the carrier further includes tetragonal zirconium oxide, and wherein a mass ratio of the tetragonal zirconium oxide to the monoclinic zirconium oxide is 3 or less.

[5] The alcohol production method according to any one of [1] to [4], wherein the carrier is zirconium oxide.

[6] The alcohol production method according to any one of [1] to [5], wherein the carrier has a specific surface area of 30 $m^2/g$ or more.

[7] The alcohol production method according to any one of [1] to [6], wherein the metal component includes one or more elements selected from elements of Groups 13 to 15 in the third and higher periods of the periodic table, the one or more elements being used as a second component.

[8] The alcohol production method according to [7], wherein a mass ratio of the elements used as the second component to the rhenium element included in the metal component is 0.1 or more and 3 or less.

[9] The alcohol production method according to [7] or [8], wherein the metal component includes germanium that is an element used as the second component.

[10] A catalyst for producing an alcohol by hydrogenation of a carbonyl compound, the catalyst comprising a carrier including zirconium oxide and a metal component supported on the carrier, the metal component including rhenium having an average valence of 4 or less.

[11] The catalyst for producing an alcohol by hydrogenation of a carbonyl compound according to [10], wherein the carrier includes at least monoclinic and/or tetragonal zirconium oxide.

[12] The catalyst for producing an alcohol by hydrogenation of a carbonyl compound according to [11], wherein the carrier includes at least monoclinic zirconium oxide.

[13] The catalyst for producing an alcohol by hydrogenation of a carbonyl compound according to [12], wherein a mass ratio of tetragonal zirconium oxide to the monoclinic zirconium oxide in the zirconium oxide is 3 or less.

[14] The catalyst for producing an alcohol by hydrogenation of a carbonyl compound according to any one of [10] to [13], wherein the carrier is zirconium oxide.

[15] The catalyst for producing an alcohol by hydrogenation of a carbonyl compound according to any one of [10] to [14], wherein the carrier has a specific surface area of 30 $m^2/g$ or more.

[16] The catalyst for producing an alcohol by hydrogenation of a carbonyl compound according to any one of [10] to [15], wherein the metal component includes one or more elements selected from elements of Groups 13 to 15 in the third and higher periods of the periodic table, the one or more elements being used as a second component.

[17] The catalyst for producing an alcohol by hydrogenation of a carbonyl compound according to [16], wherein a mass ratio of the elements used as the second component to the rhenium element included in the metal component is 0.1 or more and 3 or less.

[18] The catalyst for producing an alcohol by hydrogenation of a carbonyl compound according to [16] or [17], wherein the metal component includes germanium that is an element used as the second component.

[19] A method for producing a catalyst including a metal component including rhenium having an average valence of 4 or less and a carrier supporting the metal component, the carrier including zirconium oxide, the method comprising producing the catalyst by the steps of:

(i) supporting the metal component on the carrier;
(ii) subjecting resulting metal-supported material to a reduction treatment with a reducing gas; and
(iii) performing oxidation subsequent to the reduction treatment.

[20] The method for producing a catalyst according to [19], wherein the carrier includes at least monoclinic and/or tetragonal zirconium oxide.

Advantageous Effects of Invention

According to the present invention, the use of the specific high-activity catalyst that includes a metal component including rhenium serving as a catalytic activity component and a carrier that supports the metal component and includes zirconium oxide enables an alcohol to be produced at a high yield with high selectivity by the hydrogenation reaction of a carbonyl compound, while reducing the above-described various side reactions to a sufficient degree.

The catalyst according to the present invention may increase catalytic activity substantially without using any of the noble metals of Groups 8 to 10 of the periodic table, which has been an issue with the rhenium catalysts known in the related art. The catalyst according to the present invention also enables the production of an alcohol from a carbonyl compound while side reactions, such as the esterification reaction of the carboxylic acid used as a raw material with the alcohol produced and a defunctionalization reaction due to the dehydration and hydrogenation of the alcohol produced, which significantly occurs particularly at a later stage of the reaction, are reduced to sufficient degrees. These advantages become significant in the case where the catalyst has been reduced with a reducing gas, such as hydrogen, and subsequently subjected to an oxidative stabilization treatment with oxygen, air, or the like.

In the case where the catalyst according to the present invention is subjected to an oxidative stabilization treatment, the catalyst can be handled in air and may have excellent catalytic activity and excellent reaction selectivity. Furthermore, the catalyst may be easy to handle in the transportation or storage of the catalyst, the charging of the catalyst to a reaction container in the production of alcohols, the regeneration of the catalyst, or the like.

The catalyst according to the present invention also enables a hydroxycarboxylic acid to be produced with high selectively using a polyvalent carboxylic acid as a raw material by converting some of the carboxylic acid functional groups into alcohol functional groups.

DESCRIPTION OF EMBODIMENTS

Embodiments of the present invention are described below in detail. The elements described below are merely an example (typical example) of an embodiment of the present invention. The present invention is not limited by the description and may be modified within the scope of the present invention.

In the present invention, catalytic components supported on a carrier (e.g., rhenium; the elements of Groups 13 to 15 in the third and higher periods of the periodic table, such as aluminum, gallium, indium, silicon, germanium, tin, antimony, and bismuth; and optional metal elements of Groups 8 to 10 of the periodic table, such as ruthenium) may be referred to collectively as "metal component".

The term "periodic table" used herein refers to the long form of periodic table (Nomenclature of Inorganic Chemistry IUPAC Recommendations 2005).

A material produced by supporting the metal components on a carrier may be referred to as "metal-supported material".

A catalyst produced by reducing the metal-supported material may be referred to as "metal-supported catalyst".

In the present invention, the expression "metal component supported on a carrier" means a metal component included in the catalyst.

The content of rhenium atoms in the catalyst can be determined by known analysis methods, such as inductively coupled plasma mass spectrometry (ICP-MS), inductively coupled plasma atomic emission spectrometry (ICP-AES), atomic absorption spectrometry (AAS), and X-ray fluorescence analysis (XRF).

In the case where ICP-MS, ICP-AES, and AAS are used, the sample is formed into a solution in a pretreatment conducted in combination with the analysis.

The type of the analysis method used is not limited since an appropriate analysis method varies by the element subjected to the quantitative analysis, the concentration of the element, and the accuracy required for the analysis.

In the present invention, the quantitative analysis of rhenium atoms included in the catalyst is conducted using inductively coupled plasma atomic emission spectrometry, atomic absorption spectrometry, or both inductively coupled plasma atomic emission spectrometry and atomic absorption spectrometry in order to determine the content of rhenium atoms in the catalyst.

In the present invention "% by weight" and "% by mass" are synonymous with each other, and "element" and "atom" are synonymous with each other.

The catalyst according to the present invention is used as a hydrogenation catalyst when an alcohol is produced from a carbonyl compound.

In the present invention, a carbonyl compound is defined as a compound that includes a carbon-oxygen double bond (C=O), and an alcohol is defined as a compound produced by converting the carbonyl compound into an alcohol functional group (OH).

Therefore, in the present invention, in the case where a carbonyl compound used as a raw material includes plural carbon-oxygen double bonds, a compound produced by converting at least one of the carbon-oxygen double bonds into an alcohol functional group is defined as an alcohol.

[Catalyst According to Present Invention]

A catalyst according to the present invention (hereinafter, may be referred to simply as "the catalyst") includes a metal component including rhenium having an average valence of 4 or less and a carrier that supports the metal component and includes zirconium oxide.

The catalyst is commonly produced by reducing a metal-supported material, on which the metal component including rhenium is supported, with a reducing gas and then preferably performing an oxidative stabilization treatment.

<Metal Component>

The metal component supported on the catalyst may be any metal component including rhenium; a constituent of the metal component which is other than rhenium is not limited.

Rhenium supported on the catalyst normally exists as a mixture of rhenium species having different valences. A catalyst according to a preferable embodiment of the present invention includes the rhenium species having different valences and zirconium oxide supporting the rhenium species. The ratio of the total content of low-valent rhenium species having a valence of 3 or less in the catalyst to the content of all the rhenium species having different valences in the catalyst is preferably equal to or more than a predetermined value. The above ratio is preferably 30 mol % or more, is more preferably 40 mol % or more, is further preferably 50 mol % or more, is particularly preferably 60 mol % or more, and is especially preferably 70 mol % or more. The upper limit for the ratio of the total content of low-valent rhenium species having a valence of 3 or less to the content of all the rhenium species having different valences is not limited; the above ratio is 100 mol % or less.

The above ratio may be preferably 90 mol % or less from the viewpoint of ease of handling.

The average valence of the rhenium atoms included in the catalyst is commonly 4 or less, is more preferably 3 or less, and is further preferably 2 or less. The average valence of the rhenium atoms included in the catalyst is commonly 0.0 or more. Since rhenium exists as a mixture of rhenium species having different valences according to a more preferable embodiment, the average valence of the rhenium atoms included in the catalyst is preferably more than 0.0, is more preferably 0.1 or more, is further preferably 0.2 or more, and is particularly preferably 0.3 or more. In particular, the above average valence is preferably 0.4 or more and is more preferably 0.5 or more.

Controlling the ratio of the total content of low-valent rhenium species having a valence of 3 or less in the catalyst to the content of all the rhenium species having different valences in the catalyst such that the average valence of the rhenium atoms falls within the appropriate range enables a sufficiently high catalytic activity to be achieved in the hydrogenation catalytic reaction of a carbonyl compound. This prevents, for example, an excessive increase in the size of the reactor used and makes it possible to produce an alcohol from a carbonyl compound while reducing side reactions, such as the esterification reaction of the carboxylic acid used as a raw material with the alcohol produced and a defunctionalization reaction due to the dehydration and hydrogenation of the alcohol produced, which significantly occurs particularly at a later stage of the reaction.

The presence of the rhenium species having different valences and the ratio between the contents of the rhenium species are commonly determined by X-ray photoelectron spectroscopy (XPS).

The average valence of the rhenium atoms is commonly determined on the basis of an X-ray absorption near-edge structure (XANES) spectrum.

The reason for which the use of a metal-supported catalyst that includes a component including low-valent rhenium species (hereinafter, this component may be referred to as "rhenium component") supported thereon, that is, a metal-supported catalyst produced by adjusting the average valence of the rhenium atoms to be 4 or less by controlling the proportion of the total content of low-valent rhenium species having a valence of 3 or less, increases catalytic activity and enhances reaction selectivity is presumably as follows.

Since the low-valent rhenium component has a high reducing ability, a hydride species, which serves as a catalytic activity species, is likely to be produced. This increases hydrogenation catalytic ability. Furthermore, the Lewis acidity unique to rhenium is reduced. This reduces the esterification reaction of the carboxylic acid used as a raw material with the alcohol produced and the dehydration reaction of the alcohol produced.

Supporting the rhenium component on a carrier including zirconium oxide, in particular, a carrier including zirconium oxide with a specific crystal system, or specifically, a carrier including monoclinic zirconium oxide, markedly stabilizes the low-valent rhenium component supported on the carrier due to the interaction between the supported rhenium species and the carrier, which is described below.

From the viewpoint of the above interaction, in the present invention, the combination of zirconium oxide and the rhenium component having a specific average valence is an important issue for producing the catalyst.

The amount of rhenium supported on the catalyst is not limited. The mass ratio of the rhenium atoms to the total mass of the catalyst is commonly 0.5% by mass or more, is preferably 1% by mass or more, is more preferably 3% by mass or more; and is commonly 30% by mass or less, is preferably 20% by mass or less, is more preferably 10% by mass or less, and is further preferably 8% by mass or less.

Adjusting the amount of rhenium supported on the catalyst to fall within the above range makes it easy to adjust the average valence of rhenium included in the catalyst to be 4 or less. In addition, the mass ratio between the rhenium species having different valences is readily adjusted to be the above preferable value. Thus, sufficiently high catalytic activity may be achieved. This prevents, for example, an excessive increase in the size of the reaction container used. Furthermore, side reactions, such as a reaction that reduces the number of carbons of the resulting alcohol due to decarboxylation, a defunctionalization reaction associated with dehydration and hydrogenation of the reaction product, and an esterification reaction of the carboxylic acid used as a raw material with the alcohol produced, which are caused due to the aggregation of the rhenium supported, may be reduced. This further enhances reaction selectivity.

Adjusting the amount of rhenium supported on the catalyst to be equal to or less than the above upper limit not only makes it easy to adjust the average valence of all the rhenium species having different valences which are included in the catalyst to be 4 or less and adjust the mass ratio of the rhenium species having different valences to be the above preferable value, but also prevents an excessive increase in catalyst costs due to an increase in the amount of rhenium included in the catalyst.

The metal component supported on the catalyst may include rhenium serving as a first component and another metal component serving as a second component. Examples of the metal component serving as a second component include the elements of Groups 13 to 15 in the third and higher periods of the periodic table. Specific examples thereof include one or more elements selected from the group consisting of aluminum, gallium, indium, silicon, germanium, tin, antimony, and bismuth. Among these, one or more metals selected from the group consisting of silicon, indium, germanium, and tin are preferable. Germanium and/or tin is more preferable. Germanium is further preferable.

In the case where rhenium is used in combination with the second component, the mass ratio of the atoms of the second component to the rhenium atoms is not limited. In order to increase the advantageous effects of the second component, the above mass ratio is commonly 0.1 or more and is preferably 0.5 or more; and is commonly 10 or less, is preferably 5 or less, is more preferably 3 or less, and is particularly preferably 2 or less.

In the case where plural metal components are supported on the carrier, the mass ratio between the atoms of the supported metals may be calculated on the basis of the metal component included in the catalyst, as in the method for analyzing the content of the supported metal in the catalyst which is described above. For example, the mass ratio between the rhenium atoms and the atoms of the second component may be determined by any of the analysis methods known in the related art, such as inductively coupled plasma mass spectrometry (ICP-MS), inductively coupled plasma atomic emission spectrometry (ICP-AES), atomic absorption spectrometry (AAS), and X-ray fluorescence analysis (XRF), as in the method for analyzing the content of the supported metal in the catalyst which is described above. Some of the elements that correspond to the second component, that is, the atoms of Groups 13 to 15 in the third and higher periods of the periodic table, which are considered as an impurity may be excluded from the above calculation.

In the case where the catalyst includes the second component, appropriately selecting the type of the second component and the ratio of the amount of the second component supported to the amount of the rhenium supported as described above makes it easy to adjust the average valence of all the rhenium species having different valences which are included in the catalyst to be 4 or less and to adjust the mass ratio of the rhenium species having different valences to be the above preferable value. This may reduce the side reactions, such as an esterification reaction of the carboxylic acid used as a raw material with the alcohol produced and a defunctionalization reaction associated with dehydration and hydrogenation of the reaction product, which significantly occurs particularly at a later stage of the reaction, with further effect. These advantageous effects become significant in the case where the catalyst has been reduced with a reducing gas, such as hydrogen, and subsequently subjected to an oxidative stabilization treatment with oxygen, air, or the like. Thus, the catalyst may become very easy to handle in the transportation or storage of the catalyst, the charging of the catalyst to a reaction container in the production of alcohols, or the like. For example, it may become possible to handle the catalyst in air after the catalyst has been subjected to the oxidative stabilization treatment.

The reasons for which using the second component in combination with rhenium may reduce the side reactions and enhance the reaction selectivity are not clear in detail but are considered as described below.

The addition of the second component changes the electronic state of rhenium, which serves as a hydrogenation catalytic activity component, into a low-valent state suitable for the reduction reaction of a carbonyl functional group. That is, the addition of the second component enables the average valence of rhenium included in the catalyst to be adjusted to 4 or less. Furthermore, adsorption onto the catalyst surface is increased due to the affinity of the reactant with the second component. Moreover, the adsorption orientation of the reactant on the catalyst surface may be controlled at a high level.

The catalyst according to the present invention may further include, as needed, a third component that is a metal component other than rhenium or the second component and that does not adversely affect the reactions conducted using the catalyst according to the present invention, such as a reduction reaction.

Examples of the other metal component include metal components belonging to Groups 8 to 10 of the periodic table except iron and nickel. Examples thereof include at least one metal selected from the group consisting of metal species of ruthenium, cobalt, rhodium, iridium, palladium, and platinum, which are capable of catalyzing hydrogenation.

Metals, such as iron and nickel, may elute and enter the catalyst when a metal reaction container made of SS, SUS, or the like becomes corroded in the preparation of the catalyst and/or during the reaction.

In the case where the eluted metal is precipitated on the catalyst and included in the catalyst, the metal is not defined as a metal component of the catalyst according to the present invention. In the case of elution from a reaction container made of SUS, in addition to iron, the following metals may be detected in the catalyst in trace amounts at specific contents depending on the material used.

For example, when metals enter from SUS201, nickel, chromium, and manganese may be detected in addition to iron at specific contents.

When metals enter from SUS202, nickel, chromium, and manganese may be detected in addition to iron at specific contents.

When metals enter from SUS301, nickel and chromium may be detected in addition to iron at specific contents.

When metals enter from SUS302, nickel and chromium may be detected in addition to iron at specific contents.

When metals enter from SUS303, nickel, chromium, and molybdenum may be detected in addition to iron at specific contents.

When metals enter from SUS304, nickel and chromium may be detected in addition to iron at specific contents.

When metals enter from SUS305, nickel and chromium may be detected in addition to iron at specific contents.

When metals enter from SUS316, nickel, chromium, and molybdenum may be detected in addition to iron at specific contents.

When metals enter from SUS317, nickel, chromium, and molybdenum may be detected in addition to iron at specific contents.

When metals enter from SUS329J1, nickel, chromium, and molybdenum may be detected in addition to iron at specific contents.

When metals enter from SUS403, chromium may be detected in addition to iron at a specific content.

When metals enter from SUS405, chromium and aluminum may be detected in addition to iron at specific contents.

When metals enter from SUS420, chromium may be detected in addition to iron at a specific content.

When metals enter from SUS430, chromium may be detected in addition to iron at a specific content.

When metals enter from SUS430LX, chromium, titanium, and niobium may be detected in addition to iron at a specific content.

When metals enter from SUS630, nickel, chromium, copper, and niobium may be detected in addition to iron at specific contents.

In the case where metals, such as iron and nickel, become eluted from a reaction container made of SS, SUS, or the like due to corrosion and enter the catalyst, the content of the metal component in the catalyst is considered as the content of the metal component in the catalyst which excludes the iron content and the content of the above-described metals mixed at specific contents, which is determined by the material of which the reaction container is made. In particular, in the case where the amount of metal species considered to have entered the catalyst from the reaction container is small, the metals may be considered negligible in the calculation of the content of the metal component in the catalyst.

The catalyst may include a third component that is a metal component belonging to a group other than Groups 8 to 10 of the periodic table. Examples of such a metal component include at least one metal selected from the group consisting of metal species of silver, gold, molybdenum, tungsten, aluminum, and boron. The term "metal species" used herein includes semimetal.

Among the above third components, at least one metal selected from ruthenium, cobalt, rhodium, iridium, palladium, platinum, gold, molybdenum, and tungsten is preferable; at least one metal selected from ruthenium, cobalt, rhodium, iridium, palladium, platinum, molybdenum, and tungsten is more preferable; at least one metal selected from ruthenium, iridium, palladium, and platinum is particularly preferable; and ruthenium is most preferable.

In the case where the third component is selected from rare and expensive metals of Groups 8 to 10 of the periodic table except iron and nickel, the atomic mass ratio of the third component included in the catalyst to the rhenium atoms is commonly less than 0.2, is preferably 0.15 or less, is more preferably 0.1 or less, is further preferably less than 0.1, and is most preferably 0.0.

That is, it is preferable that the catalyst according to the present invention substantially do not include any of the rare and expensive metals of Groups 8 to 10 of the periodic table other than iron or nickel.

Adjusting the content of the third component appropriately as described above may enhance the reaction selectivity in the hydrogenation catalytic reaction of a carbonyl compound and reduce the costs of production of the catalyst.

In the case where the third component is selected from the metals other than the noble metals of Groups 8 to 10 of the periodic table, the atomic mass ratio of the third component included in the catalyst to the rhenium atoms is commonly 10 or less, is preferably 5 or less, is more preferably 1 or less, and is further preferably 0.5 or less. When the above additional metal components are used in an appropriate combination at adequate contents, high catalytic activity may be achieved while high selectivity is maintained.

In order to further increase the activity of the catalyst, reaction selectivity, and the like, the catalyst may include compounds of one or more alkali metal elements selected from the group consisting of lithium, sodium, potassium, rubidium, and cesium; compounds of one or more alkaline-earth metal elements selected from the group consisting of magnesium, calcium, strontium, and barium; and compounds of one or more halogen elements selected from the group consisting of fluorine, chlorine, bromine, and iodine, in addition to the metal component described above. In such a case, the ratio between the additional components and the rhenium component is not limited.

<Carrier>

The catalyst includes a carrier including zirconium oxide. The zirconium oxide is preferably monoclinic zirconium oxide, tetragonal zirconium oxide, or a mixture thereof and is more preferably monoclinic zirconium oxide.

It is known that zirconium oxide generally exists in the forms of amorphous (temperature at which the crystals are stable: 250° C. to 430° C.), metastable tetragonal (the above temperature: 430° C. to 650° C.), monoclinic (the above temperature: 650° C. to 1000° C.), stable tetragonal (the above temperature: 1000° C. to 1900° C.), and cubic (the above temperature: 1900° C. to 2715° C.)

The higher the temperature at which the zirconium oxide carrier is calcined and the larger the amount of time during which the carrier is calcined, the smaller the specific surface area of the carrier.

In general, it is preferable to use a carrier having a larger specific surface area for enhancing the catalytic activity of the metal-supported catalyst. From this viewpoint, the zirconium oxide used as a carrier is preferably amorphous zirconium oxide, metastable tetragonal zirconium oxide, monoclinic zirconium oxide, tetragonal zirconium oxide, and cubic zirconium oxide in order of preference, for achieving high catalytic activity.

The catalyst preferably includes crystalline zirconium oxide and particularly preferably includes monoclinic and/or tetragonal zirconium oxide. Among these, monoclinic zirconium oxide is preferably included in the catalyst.

The carrier included in the catalyst according to a more preferable embodiment may be any carrier that includes monoclinic zirconium oxide; the carrier may include zirconium oxide other than monoclinic zirconium oxide, that is, any of metastable tetragonal zirconium oxide, stable tetragonal zirconium oxide, and cubic zirconium oxide. Hereinafter, metastable tetragonal and stable tetragonal are referred to collectively as "tetragonal".

Examples of the raw material for the carrier used for preparing the catalyst include zirconium hydroxide, zirconium oxyhydroxide, zirconium chloride, zirconium oxychloride, zirconium sulfate, zirconium acetate, zirconium oxyacetate, and a mixture thereof. The crystalline zirconium oxide included in the catalyst may be derived from amorphous zirconium oxide, monoclinic zirconium oxide, tetragonal zirconium oxide, and the like prepared separately. In another case, after a metal has been supported on any of the above raw materials for the carrier by a common method, the resulting metal-supported material may be converted into a carrier having a preferable crystal system by heating.

The carrier may include a substance other than zirconium oxide such that the advantageous effects of the present invention are not impaired. It is preferable that the carrier included in the catalyst consist of zirconium oxide, except the impurities inevitable in the production of the carrier. In the case where zirconium oxide including plural crystal systems is used as a carrier, calcination needs to be performed at high temperatures as described above. In addition, it is preferable to minimize the content of cubic zirconium oxide from the viewpoint of specific surface area. Therefore, in the case where zirconium oxide including plural crystal systems is used as a carrier, it is preferable to use monoclinic zirconium oxide in combination with tetragonal zirconium oxide.

Since the catalyst according to a more preferable embodiment includes monoclinic zirconium oxide, the mass ratio of tetragonal zirconium oxide to monoclinic zirconium oxide is commonly 5 or less, is preferably 4 or less, is more preferably 3 or less, is further preferably 2 or less, is particularly preferably 1 or less, and is especially preferably 0.4 or less.

Monoclinic zirconium oxide that does not include tetragonal zirconium oxide is one of the catalysts according to the particularly preferable embodiments.

The mass ratio of tetragonal zirconium oxide to monoclinic zirconium oxide is determined by X-ray diffraction measurement or the like. The above mass ratio may be calculated, for example, on the basis of the intensity of a peak at 30°±0.5°, which is unique to tetragonal zirconium oxide, and the intensity of a peak at 28.2°±0.5°, which is unique to monoclinic zirconium oxide, measured using Cu—Kα radiation, by the method described below.

It is preferable to use monoclinic zirconium oxide as a carrier included in the catalyst and/or to adjust the mass ratio of tetragonal zirconium oxide to monoclinic zirconium oxide to fall within the above range. This is because, in such a case, it becomes easy to adjust the average valence in the catalyst to be 4 or less and adjust the mass ratio of the rhenium species having different valences to be the above preferable value and, consequently, the hydrogenation catalytic activity power of the catalyst in the hydrogenation catalytic reaction of a carbonyl compound may be markedly enhanced. In such a case, the catalyst produces high catalytic activity as a result of being used in combination with the specific zirconium oxide carrier. Furthermore, it becomes possible to handle the catalyst in air. That is, the catalyst may become very easy to handle in the transportation or storage of the catalyst, the charging of the catalyst to a reaction container in the production of alcohols, or the like.

The reasons for which supporting the rhenium component on a carrier including crystalline zirconium oxide, which is particularly preferably monoclinic zirconium oxide, markedly enhances the hydrogenation catalytic activity power of the catalyst in the hydrogenation catalytic reaction of a carbonyl compound are considered as described below.

Crystalline zirconium oxide has an uppermost surface having a stable structure (crystal plane). This enables the low-valent rhenium atoms to be stabilized and dispersed to a high degree due to the interaction between the rhenium component and zirconium oxide. This makes it easy to adjust the average valence of rhenium included in the catalyst to be 4 or less and adjust the mass ratio of the rhenium species having different valences to be the above preferable value. In particular, in the case where monoclinic zirconium oxide is used, the low-valent rhenium atoms may be further stabilized and dispersed to a further high degree due to the interaction between the rhenium component and the zirconium oxide, compared with the case where zirconium oxide having a crystal system other than a monoclinic system is used. This enables the electronic state of the rhenium atoms, which serve as a hydrogenation catalytic activity component, to be fixed at a low valent, that is, such that the average valence of the rhenium is 4 or less, which is suitable for the reduction reaction of a carbonyl functional group. As a result, it becomes possible to maintain a larger amount of low-valent rhenium atoms to be dispersed at a high level. Furthermore, the aggregation and oxidation resistance of the low-valent rhenium atoms may be enhanced. For the above reasons, the above advantageous effects may be produced.

The zirconium oxide-containing carrier according to the present invention may be used in combination with the inert carrier described below. In the case where the inert carrier is used in combination with the carrier according to the present invention, the combination of the inert carrier and the carrier according to the present invention and the mixing ratio therebetween are not limited. The carrier used in the present invention is preferably composed primarily of zirconium oxide. The expression "composed primarily of" used herein means that the ratio of the mass of zirconium oxide to the total mass of the carrier is commonly 50% by mass or more, is preferably 70% by mass or more, and is more preferably 90% to 100% by mass.

The inert carrier is defined as a carrier that substantially does not include any of the metals of Groups 8 to 12 of the periodic table which are selected from the group consisting of iron, ruthenium, cobalt, rhodium, iridium, nickel, palladium, platinum, copper, and zinc, as well as chromium, and rhenium, which are metals having catalytic activity. If the carrier includes the above metals in an excessively large amount, catalytic active sites may be formed on the carrier in the hydrogenation reaction of a carbonyl compound. This may cause, for example, side reactions, such as the esterification reaction of the carboxylic acid used as a raw material with the alcohol produced and a defunctionalization reaction due to the dehydration and hydrogenation of the alcohol produced, and consequently adversely affect the reaction selectivity. Therefore, it is preferable that the carrier substantially do not include any of the above catalytic activity metals.

The expression "carrier substantially does not include any of the above catalytic activity metals" used herein means that the amount of the metals included in the carrier to the total mass of the carrier is 5% by mass or less, is preferably 1% by mass or less, and is more preferably 0.1% by mass or less. The content of the above metals in the carrier can be determined as in the analysis of the content of the supported metal in the catalyst, using known analysis methods, such as inductively coupled plasma mass spectrometry (ICP-MS), inductively coupled plasma atomic emission spectrometry (ICP-AES), atomic absorption spectrometry (AAS), and X-ray fluorescence analysis (XRF).

Examples of another inert carrier that can be used in combination with zirconium oxide include one or more compounds selected from graphite, active carbon, silicon carbide, silicon nitride, aluminum nitride, boron nitride, boron oxide, aluminum oxide (alumina), silicon oxide (silica), titanium oxide, lanthanum oxide, cerium oxide, yttrium oxide, hafnium oxide, niobium oxide, magnesium silicate, calcium silicate, magnesium aluminate, calcium aluminate, aluminosilicate, aluminosilicophosphate, aluminophosphate, magnesium phosphate, calcium phosphate, strontium phosphate, apatite hydroxide (calcium hydroxyphosphate), apatite chloride, apatite fluoride, calcium sulfate, barium sulfate, and barium carbonate.

The above carriers may be used alone or in combination of two or more. In the case where the above carriers are used in combination of two or more, the combination of the carriers and the mixing ratio therebetween are not limited. The above compounds can be used in a form similar to a mixture of the compounds, a composite compound, or a double salt.

The specific surface area of the carrier used in the present invention is preferably 30 $m^2/g$ or more, is more preferably 40 $m^2/g$ or more, and is further preferably 50 $m^2/g$ or more; and is preferably 500 $m^2/g$ or less and is more preferably 350 $m^2/g$ or less. The larger the specific surface area of the carrier, the higher the ease of adjusting the average valence of the rhenium species having different valences which are included in the catalyst to be 4 or less, the higher the ease of adjusting the mass ratio of the rhenium species having different valences to be the above preferable value, and the higher the catalytic activity. Therefore, it is suitable to use a carrier having a larger specific surface area. From the above viewpoint, it may be preferable to use metastable tetragonal zirconium oxide in combination with monoclinic zirconium oxide.

The specific surface area of the carrier is generally calculated from the amount of nitrogen adsorbed on the carrier using the BET equation.

As described above, in the present invention, it may be important to control the balance between the content of monoclinic zirconium oxide, which intrinsically has a high hydrogenation catalytic activity power in the hydrogenation catalytic reaction of a carbonyl compound, and the specific surface area of the zirconium oxide used.

While zirconium oxide according to a most preferable embodiment is monoclinic zirconium oxide having a large specific surface area, the preparation of monoclinic zirconium oxide requires calcination performed at relatively high temperatures and, depending on the preparation conditions, for a long period of time, which reduces specific surface area. Therefore, it may be difficult to prepare the optimal zirconium oxide. Thus, in the present invention, adjusting the content of monoclinic zirconium oxide and the specific surface area of zirconium oxide appropriately to fall within the above ranges may markedly enhance the hydrogenation catalytic activity power in the hydrogenation catalytic reaction of a carbonyl compound.

The specific surface area of the catalyst that includes the carrier having the suitable specific surface area is not limited and varies by the type of zirconium oxide used and type of the carrier used in combination with zirconium oxide. The specific surface area of the catalyst is preferably 30 m$^2$/g or more, is more preferably 40 m$^2$/g or more, and is further preferably 50 m$^2$/g or more; and is preferably 500 m$^2$/g or less and is more preferably 350 m$^2$/g or less. The larger the specific surface area of the catalyst, the higher the catalytic activity. Therefore, a catalyst having a larger specific surface area is suitably used. The specific surface area of the catalyst is calculated from the amount of nitrogen adsorbed on the catalyst using the BET equation.

The shape and size of the carrier particles used in the present invention are not limited. When the shape of the carrier particles is converted into a spherical shape, the average particle size of the carrier is commonly 0.1 μm or more, is preferably 1 μm or more, is more preferably 5 μm or more, is further preferably 50 μm or more, is commonly 5 mm or less, and is preferably 4 mm or less. The particle size of the carrier is measured in accordance with Test sieving described in JIS Standard JIS Z8815 (1994). In the case where the shape of a carrier particle is not spherical, the volume of the carrier particle is measured, the diameter of a spherical particle having the same volume as the carrier particle is calculated, and the diameter of the spherical particle is considered the diameter of the carrier particle. When the average particle size of the carrier falls within the above range, the activity of the catalyst per unit mass is high, and ease of handling of the catalyst is further increased.

In the case where the reaction conducted using the catalyst is a complete mixing reaction, the average particle size of the carrier is commonly 0.1 μm or more, is preferably 1 μm or more, is more preferably 5 μm or more, is further preferably 50 μm or more, is commonly 3 mm or less, and is preferably 2 mm or less. It is preferable to minimize the average particle size of the carrier because the smaller the average particle size of the carrier, the higher the activity of the catalyst per unit mass. It is preferable to set the average particle size of the carrier to be equal to or more than the lower limit, because setting the average particle size of the carrier to be equal to or more than the lower limit may make it easy to separate the reaction liquid and the catalyst from each other.

In the case where the reaction conducted using the catalyst is a fixed-bed reaction, the average particle size of the carrier is commonly 0.5 mm or more and 5 mm or less, is preferably 4 mm or less, and is more preferably 3 mm or less. Setting the average particle size of the carrier to be equal to or more than the lower limit may prevent the occurrence of pressure difference during the operating time. Setting the average particle size of the carrier to be equal to or less than the upper limit enables the reaction activity to be maintained at a high level.

As a carrier used in the present invention, an equivalent commercial product may be used directly.

Zirconium oxide may be produced by the hydrolysis of a zirconium compound, such as zirconium oxychloride, zirconium oxynitrate, or zirconium propoxide, or by neutralizing the zirconium compound with ammonia water or the like to produce zirconium hydroxide or amorphous zirconium oxide hydrate and subsequently performing calcination in air.

The calcination temperature is commonly 450° C. or more, is preferably 500° C. or more, is more preferably 550° C. or more, is further preferably 600° C. or more, and is particularly preferably 650° C. or more; and is commonly 2500° C. or less, is preferably 1900° C. or less, and is more preferably 1000° C. or less. Performing calcination within the above temperature range enables the crystal phase preferable in the present invention to be readily formed. Furthermore, a reduction in the surface area of zirconium oxide which occurs due to an excessively high calcination temperature may be limited. In addition, a reduction in the content of monoclinic zirconium oxide may be limited.

The lower limit for the calcination time is not limited because the calcination time varies with the calcination temperature. The calcination time is commonly 1 hour or more and is preferably 3 hours or more. The upper limit for the calcination time is also not limited. The calcination time is commonly 100 hours or less, is preferably 50 hours or less, and is more preferably 10 hours or less.

[Method for Producing the Catalyst]

The method for producing the catalyst commonly includes the following steps.

(i) a step in which the metal components are supported on the carrier (hereinafter, this step is referred to as "metal supporting step")

(ii) a step in which the resulting metal-supported material is subjected to a reduction treatment using a reducing gas (hereinafter, this step is referred to as "reduction treatment step")

(iii) a step in which oxidation is performed subsequent to the reduction treatment (hereinafter, this step is referred to as "oxidative stabilization step")

Each of the above steps is described below.

<(i) Metal Supporting Step>

The metal supporting step is a step in which required amounts of the above-described metal components are supported on the above-described carrier in order to prepare a metal-supported material. The method for supporting the metal components on the carrier is not limited, and known methods can be used. For supporting the metal components on the carrier, a solution or dispersion liquid containing metal-containing compounds that are raw materials for the metal components can be used.

The method for supporting the metal components on the carrier is not limited. Various impregnation methods may be used commonly. Examples thereof include the following methods:

an adsorption method in which metal ions are caused to adsorb to the carrier in an amount equal to or less than the saturation amount of the metal ions adsorbed by using the ability of the metal ions to adsorb to the carrier;

an equilibrium adsorption method in which the carrier is immersed in the solution containing an amount of metal ions which is equal to or more than the saturation amount of the metal ions adsorbed and the excess solution is removed;

a pore-filling method in which the solution having the same volume as the pores formed in the carrier is added to the carrier and the whole amount of the solution is caused to adsorb to the carrier;

an incipient wetness method in which the solution is added to the carrier until the volume of the solution added is appropriate to the water absorption capacity of the carrier and the treatment is terminated when the surfaces of the carrier particles become uniformly wet and excess solution is not present on the surfaces of the carrier particles; an evaporation-to-dryness method in which the carrier is impregnated with the solution and the solvent is removed by evaporation while the solution is stirred; and a spray method in which the carrier is dried and the solution is sprayed to the dried carrier.

Among these, the pore-filling method, the incipient wetness method, the evaporation-to-dryness method, and the spray method are preferable, and the pore-filling method, the incipient wetness method, and the evaporation-to-dryness method are more preferable.

Using the above preparation methods enables rhenium, the optional second component, the optional third component, and the other metal components to be supported on the carrier while being relatively uniformly dispersed on the carrier.

The rhenium metal-containing compounds used are not limited and may be selected appropriately in accordance with the supporting method used. Examples thereof include halides, such as a chloride, a bromide, and an iodide; mineral acid salts, such as a nitric acid salt and a sulfuric acid salt; metal hydroxides; metal oxides; metal-containing ammonium salts; organic-group-containing compounds, such as an acetic acid salt and a metal alkoxide; and metal complexes. Among these, halides, mineral acid salts, metal hydroxides, metal oxides, metal-containing ammonium salts, and organic-group-containing compounds are preferable, and halides, mineral acid salts, metal oxides, metal-containing ammonium salts, and organic-group-containing compounds are more preferable. The above compounds may be used alone or in combination of two or more in a required amount.

When the rhenium metal-containing compounds are supported on the carrier, the metal-containing compounds may be dissolved or dispersed in a solvent and the resulting solutions and dispersion liquids may be used in any of the above supporting methods. The type of the solvent used in this step is not limited and may be any type of solvent in which the metal-containing compounds can be dissolved or dispersed and which does not adversely affect the calcination and hydrogen reduction of the metal-supported material and the hydrogenation reaction in which the catalyst is used, which are conducted in the subsequent step. Examples of the solvent include ketone solvents, such as acetone, alcohol solvents, such as methanol and ethanol, ether solvents, such as tetrahydrofuran and ethylene glycol dimethyl ether, and water. The above solvents may be used alone or in the form of a mixed solvent. Among the above solvents, water is preferably used because water is inexpensive and the solubility of the raw materials, that is, the metal-containing compounds, in water is high.

When the rhenium metal-containing compounds are dissolved or dispersed in the solvent, various additives may be optionally used in addition to the solvent. For example, using a solution of carboxylic acid and/or a carbonyl compound may improve the dispersibility of each of the metal components on the carrier which is achieved when the metal components are supported on the carrier, as described in Japanese Unexamined Patent Application Publication No. 10-15388.

The metal-supported material may be dried as needed. It is preferable to subject the metal-supported material to a reduction treatment step after the metal-supported material has been dried and subsequently calcined as needed, for the following reason: if the metal-supported material is subjected to the subsequent reduction treatment without being dried, it may become difficult to adjust the average valence of rhenium included in the catalyst to be 4 or less and, consequently, the catalyst may have low reaction activity.

The method for drying the metal-supported material is not limited and may be any method capable of removing the solvent and the like used for supporting the metal components on the carrier. Commonly, the metal-supported material is dried in a stream of gas or at a reduced pressure. The gas used for drying the metal-supported material may be air or an inert gas, such as a nitrogen gas or an argon gas.

The pressure at which the metal-supported material is dried is not limited. Commonly, the metal-supported material is dried at normal pressure or a reduced pressure.

The temperature at which the metal-supported material is dried is commonly, but not limited to, 300° C. or less, is preferably 250° C. or less, is more preferably 200° C. or less, and is commonly 80° C. or more.

After the metal-supported material has been dried, the metal-supported material may be calcined as needed. Calcination the metal-supported material makes it easy to adjust the average valence of rhenium included in the catalyst to be 4 or less and increases the likelihood of the catalyst having a high catalytic activity and excellent reaction selectivity. The calcination of the metal-supported material is commonly performed in air. For example, the calcination of the metal-supported material may be performed by heating the metal-supported material in an air stream at a predetermined temperature for a predetermined amount of time. The calcination may be performed under a stream of a gas diluted with an inert gas, such as nitrogen, or under a stream of the inert gas.

The temperature at which the metal-supported material is calcined is commonly, but not limited to, 100° C. or more, is preferably 250° C. or more, is more preferably 400° C. or more, is commonly 1000° C. or less, is preferably 700° C. or less, and is more preferably 600° C. or less.

The amount of time during which the metal-supported material is calcined, which varies with the calcination temperature, is commonly 30 minutes or more, is preferably 1 hour or more, is more preferably 2 hours or more, is commonly 40 hours or less, is preferably 30 hours or less, and is more preferably 10 hours or less.

<(ii) Reduction Treatment Step>

The metal-supported material is commonly subjected to a reduction treatment using a reducing gas. In the reduction treatment, a known method, such as liquid-phase reduction or a gas-phase reduction, may be used.

The reducing gas used in the reduction treatment step is not limited and may be any gas having a reducing power. Examples of the reducing gas include hydrogen, methanol, and hydrazine. The reducing gas is preferably hydrogen.

In the case where a hydrogen-containing gas is used as a reducing gas, the hydrogen concentration in the hydrogen-containing gas is not limited. The hydrogen concentration in the hydrogen-containing gas may be 100% by volume. In another case, the hydrogen-containing gas may be diluted with an inert gas. The term "inert gas" used herein refers to a gas unreactive with the metal-supported material or a hydrogen gas, such as a nitrogen gas, an argon gas, or water vapor. Commonly, a nitrogen gas is used as an inert gas.

The hydrogen concentration in the reducing gas (hydrogen-containing gas) diluted with an inert gas is commonly 5% by volume or more, is preferably 15% by volume or more, is more preferably 30% by volume or more, and is further preferably 50% by volume or more relative to the all the gas components. It is possible to use a hydrogen-containing gas having a low hydrogen concentration at the initial stage of reduction and gradually increase the hydrogen concentration in the hydrogen-containing gas over the course of reduction.

The amount of time required for the reduction treatment, which varies with the amounts of the metal-supported material and the like that are to be treated and the type of the apparatus or the like used, is commonly 7 minutes or more, is preferably 15 minutes or more, is more preferably 30 minutes or more, is commonly 40 hours or less, is preferably 30 hours or less, and is more preferably 10 hours or less.

The temperature at which the reduction treatment is performed is commonly 100° C. or more, is preferably 200° C. or more, is more preferably 250° C. or more, is commonly 700° C. or less, is preferably 600° C. or less, and is more preferably 500° C. or less.

Adjusting the above reduction treatment temperature to fall within the appropriate range makes it easy to adjust the valence of rhenium to be suitable for the hydrogenation catalytic reaction of a carbonyl compound and to produce a catalyst including rhenium having an average valence of 4 or less. Furthermore, the mass ratio between the rhenium species having different valences which are included in the catalyst may be readily adjusted to be the above preferable value. Furthermore, for example, the sintering of the supported metal may be prevented and, consequently, the activity of the catalyst may be maintained at a high level.

In the reduction treatment, the reducing gas may be enclosed in the reactor or may be passed through the reactor. It is preferable to pass the reducing gas through the reactor. Passing the reducing gas through the reactor prevents the reducing gas from becoming depleted locally. In the reduction treatment, water, ammonium chloride, and the like may be produced as by-products in the rector depending on the raw materials used, and the by-products may adversely affect the metal-supported material that has not been subjected to the reduction treatment or the metal-supported catalyst, which has been subjected to the reduction treatment. Passing the reducing gas through the reactor enables the by-products to be discharged to the outside of the reaction system.

The amount of the reducing gas required by the reduction treatment is not limited and may be set such that the objects of the present invention are achieved. The amount of the reducing gas required by the reduction treatment can be set appropriately in accordance with the apparatus used, the size of the reactor used for reduction, the method for passing the reducing gas through the reactor, the method for fluidizing the catalyst, and the like.

The size of the metal-supported catalyst, which has been subjected to the reduction treatment, is not limited and basically the same as the size of the carrier.

Examples of a preferable method for performing the reduction treatment include a method in which the reducing gas is passed through the metal-supported material with a fixed bed; a method in which the reducing gas is passed through the metal-supported material that is disposed to stand on a tray or a belt; and a method in which the metal-supported material is caused to fluidize and the reducing gas is passed through the fluidized metal-supported material.

<(iii) Oxidative Stabilization Step>

In the production of the catalyst, the metal-supported catalyst, which is produced by reducing the metal-supported material, is preferably subjected to an oxidative stabilization treatment in order to control the oxidation state. Performing the oxidative stabilization treatment enables the production of a catalyst that has excellent activity and excellent selectivity and that can be handled in air.

The method for performing oxidative stabilization is not limited. Examples thereof include the following:

a method in which water is added to the metal-supported catalyst;

a method in which the metal-supported catalyst is charged into water, a method in which oxidative stabilization is performed using a gas having a low oxygen concentration which is diluted with an inert gas; and a method in which stabilization is performed using carbon dioxide.

Among the above methods, the method in which water is added to the metal-supported catalyst, the method in which the metal-supported catalyst is charged into water, and the method in which oxidative stabilization is performed using the gas having a low oxygen concentration are preferable, the method in which oxidative stabilization is performed using the gas having a low oxygen concentration is more preferable, and a method in which oxidative stabilization is performed in a stream of the gas having a low oxygen concentration is particularly preferable.

The initial oxygen concentration with which oxidative stabilization is performed using the gas having a low oxygen concentration is not limited. The oxygen concentration with which the oxidative stabilization is started is commonly 0.2% by volume or more, is preferably 0.5% by volume or more, is commonly 10% by volume or less, is preferably 8% by volume or less, and is further preferably 7% by volume or less. Adjusting the oxygen concentration at which oxidative stabilization is started to fall within the above appropriate range makes it possible to adjust the valence of rhenium to be suitable for the catalytic reaction performed in the production of an alcohol by the hydrogenation of a carbonyl compound and to adjust the mass ratio between the rhenium species having different valences which are included in the catalyst to be the above preferable value.

The gas having a low oxygen concentration is preferably prepared by diluting air with the inert gas. The inert gas used for diluting air is preferably a nitrogen gas.

Examples of a method for performing the oxidative stabilization using the gas having a low oxygen concentration include a method in which the gas having a low oxygen concentration is passed through the catalyst with a fixed bed; a method in which the gas having a low oxygen concentration is passed through the catalyst that is disposed to stand on a tray or a belt; and a method in which the catalyst is caused to fluidize and the gas having a low oxygen concentration is passed through the fluidized catalyst.

The higher the dispersibility of the supported metal on the metal-supported catalyst, the higher the rate at which the oxidative stabilization is performed and the larger the amount of oxygen used in the reaction. Therefore, the method in which the gas having a low oxygen concentration is passed through the catalyst with a fixed bed and the method in which the catalyst is caused to fluidize and the gas having a low oxygen concentration is passed through the fluidized catalyst are preferable.

The method for producing the catalyst is not limited to the above-described production method and may be any method capable of producing the catalyst. The method for producing the catalyst may include another known step such that the catalyst can be produced.

[Production of Alcohol with the Catalyst]

The catalyst is suitable as a catalyst used in the reduction reaction (hydrogenation) of a carbonyl compound. An alcohol can be produced by treating a carbonyl compound with the catalyst.

Preferable examples of the reduction reaction conducted with the catalyst include an alcohol production method which includes a step in which at least one carbonyl compound selected from the group consisting of a ketone, an aldehyde, a carboxylic acid, a carboxylic acid ester, a carboxylic acid amide, a carboxylic acid halide, and a carboxylic anhydride is reduced to produce an alcohol derived from the compound. Among the above compounds, a carboxylic acid can be directly reduced with the catalyst to form an alcohol.

The carbonyl compound that is to be subjected to the reduction reaction may be any carbonyl compound that is industrially readily available. Specific examples of the carboxylic acid and/or the carboxylic acid ester include aliphatic chain monocarboxylic acids, such as acetic acid, butyric acid, decanoic acid, lauric acid, oleic acid, linoleic acid, linolenic acid, stearic acid, and palmitic acid; aliphatic cyclic monocarboxylic acids, such as cyclohexanecarboxylic acid, naphthenic acid, and cyclopentanecarboxylic acid; aliphatic polycarboxylic acids, such as oxalic acid, malonic acid, succinic acid, methylsuccinic acid, glutaric acid, adipic acid, pimelic acid, suberic acid, sebacic acid, cyclohexanedicarboxylic acid, 1,2,4-butanetricarboxylic acid, 1,3,4-cyclohexanetricarboxylic acid, bicyclohexyldicarboxylic acid, and decahydronaphthalenedicarboxylic acid; aromatic carboxylic acids, such as phthalic acid, isophthalic acid, terephthalic acid, and trimesic acid; carboxylic acids including a furan skeleton, such as furancarboxylic acid and furandicarboxylic acid; carboxylic acid esters, such as methyl esters, ethyl esters, propyl esters, and butyl esters of the above carboxylic acids and esters of an alcohol produced by reducing a carboxylic acid; and lactones, such as γ-butyrolactone, δ-valerolactone, and ε-caprolactone.

Specific examples of the carboxylic acid amide include methyl amides and ethyl amides of the above carboxylic acids.

Specific examples of the carboxylic acid halide include chlorides and bromides of the above carboxylic acids.

Specific examples of the carboxylic anhydride include acetic anhydride, succinic anhydride, maleic anhydride, and phthalic anhydride.

Examples of the aldehyde and the ketone include benzaldehyde, propionaldehyde, acetaldehyde, 3-hydroxypropionaldehyde, furfural, hydroxymethylfurfural, acetone, benzophenone, glucose, xylose, lactose, and fructose.

The carboxylic acid and carboxylic acids constituting the carboxylic acid ester, the carboxylic acid amide, the carboxylic acid halide, and/or the carboxylic anhydride are preferably, but not limited to, chain or cyclic saturated aliphatic carboxylic acids, are more preferably carboxylic acids a portion of which excluding carboxyl groups has 20 or less carbon atoms, and are more preferably carboxylic acids having 14 or less carbon atoms.

In the present invention, among the above carbonyl compounds that are to be subjected to the reduction reaction, the carboxylic acid, the carboxylic acid ester, the carboxylic anhydride, and the aldehyde are preferable, the carboxylic acid, the carboxylic acid ester, the carboxylic anhydride, and the aldehyde are more preferable, and the carboxylic acid and the carboxylic acid ester are particularly preferable from the viewpoint of ease of availability of the raw materials. Among the above carbonyl compounds, in particular, the carboxylic acid is particularly preferable. However, the carbonyl compounds that are to be subjected to the reduction reaction are not limited to the above carbonyl compounds.

The carboxylic acid is preferably a dicarboxylic acid and is further preferably a dicarboxylic acid represented by Formula (1) below the portion of which except carboxyl groups includes 20 or less carbon atoms.

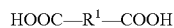　　　　　　　　　　　　　　　　(1)

(in Formula (1), $R^1$ represents an aliphatic or alicyclic hydrocarbon group that may have a substituent, the portion of the hydrocarbon group except the substituent including 1 to 20 carbon atoms)

The catalyst enables a polyvalent carboxylic acid, such as the above dicarboxylic acid, to be converted into a corresponding hydroxycarboxylic acid or polyhydric alcohol with high selectivity at a high yield. Appropriately selecting the production conditions, such as the type of catalyst used, the reaction pressure, the reaction temperature, and the amount of time the raw materials are retained, enables the ratio between the amount of the hydroxycarboxylic acid produced and the amount of the polyhydric alcohol produced to be controlled.

Other examples of particularly preferable carbonyl compounds include carboxylic acids having a furan skeleton which are derived from biomass resources, such as furandicarboxylic acid, and aldehydes, such as furfural and hydroxymethylfurfural.

Although the reduction reaction using the catalyst may be conducted in a liquid phase or gas phase, the reduction reaction using the catalyst is preferably conducted in a liquid phase. Although the reduction reaction using the catalyst in a liquid phase may be conducted without using a solvent or in the presence of a solvent, the reduction reaction using the catalyst in a liquid phase is commonly conducted in the presence of a solvent.

Examples of the solvent include, commonly, water; lower alcohols, such as methanol and ethanol; alcohols that are the reaction products; ethers, such as tetrahydrofuran, dioxane, and ethylene glycol dimethyl ether; and hydrocarbons, such as hexane, decalin, and methylcyclohexane. The above solvents may be used alone or in a mixture of two or more.

In particular, in the case where a carbonyl compound is to be reduced, it may be preferable to use a water solvent from the viewpoints of solubility and the like.

The amount of the solvent used is commonly, but not limited to, about 0.1 to 20 times by mass, is preferably 0.5 to 10 times by mass, and is more preferably about 1 to 10 times by mass the amount of the carbonyl compound used as a raw material.

The reduction reaction using the catalyst is commonly conducted in a pressurized hydrogen gas. The reaction is commonly conducted at 100° C. to 300° C. and is preferably conducted at 120° C. to 250° C. The reaction pressure is commonly 1 to 30 MPaG, is preferably 1 to 25 MPaG, and is further preferably 3 to 25 MPaG.

After the reaction has been terminated, the product of the reduction reaction using the catalyst is commonly recovered by solvent distillation, solvent distillation followed by extraction using an organic solvent, distillation, sublimation, crystallization, chromatography, or the like, which depends on the physical properties of the product.

In the case where the product is liquid at handling temperature, it is preferable to recover the product while purifying the product by distillation.

In the case where the product is solid at handling temperature, it is preferable to recover the product while purifying the product by crystallization.

It is preferable to purify the solid product by washing.

EXAMPLES

The present invention is described below further in detail with reference to Examples. The present invention is not limited by Examples below without departing from the scope of the present invention.

<Method for Analyzing Average Valence of Re>

The average valence of the rhenium atoms included in the metal-supported catalyst was calculated on the basis of an X-ray absorption near-edge structure (XANES) spectrum at the LIII absorption edge of Re. The position of the peak of the XANES spectrum was defined to be the energy position at which the first derivative was 0. The relation between peak position and valence was derived by fitting a linear function to the peak positions of Re, $ReO_2$, and $ReO_3$. The valence was calculated on the basis of the XANES peak position of the catalyst sample. The Re LIII absorption edge XANES spectrum was measured with a Si(111) double crystal monochromator by a penetration method.

<Method for Analyzing Specific Surface Area>

The specific surface area was measured using a fully automatic specific surface area measuring apparatus "AMS-1000" produced by Ohkura Riken Co., Ltd. by a single-point BET surface area measuring method in which nitrogen adsorption was performed subsequent to a pretreatment in which degassing was performed at 200° C. for 10 minutes.

<Method for Determining Mass Ratio Between Tetragonal Zirconium Oxide to Monoclinic Zirconium Oxide>

The mass ratio of tetragonal zirconium oxide to monoclinic zirconium oxide was calculated on the basis of the intensity ratio between the peaks observed in an X-ray diffraction measurement.

The relation between the ratio of the peak intensity of tetragonal crystal phase (2θ peak at about 30°) to the peak intensity of monoclinic phase (2θ peak at about 28.2°) and the mass ratio of tetragonal zirconium oxide to monoclinic zirconium oxide was derived by fitting a quadratic function to the ratios of the peak intensity of tetragonal crystal phase (2θ peak at about 30°) to the peak intensity of monoclinic phase (2θ peak at about 28.2°) of a tetragonal zirconium oxide sample, a monoclinic zirconium oxide sample, a sample prepared by mixing tetragonal zirconium oxide with monoclinic zirconium oxide at 1:1, a sample prepared by mixing tetragonal zirconium oxide with monoclinic zirconium oxide at 1:2, and a sample prepared by mixing tetragonal zirconium oxide with monoclinic zirconium oxide at 2:1. Using the above relation, the mass ratio of tetragonal zirconium oxide to monoclinic zirconium oxide was calculated from the ratio of the peak intensity of tetragonal crystal phase (2θ peak at about 30°) to the peak intensity of monoclinic phase (2θ peak at about 28.2°) of the catalyst sample.

X-ray diffraction measurement was conducted under the following conditions by charging the sample into a sample holder having a diameter of 20 mm and a depth of 0.2 mm with "D2 PHASER" produced by Bruker Corporation.

X-ray (Cu) power: 30 kv, 10 mA
Sample rotational speed: 15 rpm/min
Measurement range: 3° to 50°
Step width: 0.02°
Counting time: 0.05 sec/step
Divergence slit: 0.4 mm
Soller slit: 2.5
Air scatter sink: 1 mm Example I-1-A Ammonium perrhenate was dissolved in water. Monoclinic zirconium oxide having a specific surface area of 97 $m^2/g$ (produced by Saint-Gobain) used as a carrier was added to the resulting solution. The resulting mixture was stirred at room temperature for 1 hour. Subsequently, water was removed using an evaporator. Then, drying was performed at 100° C. for 3 hours. The resulting material was charged into a vertical calcination tube. While air was passed through the tube, a calcination treatment was performed at 500° C. for 3 hours. The resulting solid was charged into another vertical calcination tube. While a hydrogen gas was passed through the tube, a reduction treatment was performed at 500° C. for 30 minutes. Subsequently, the temperature was reduced to 30° C. Then, purging was performed with an argon gas. Thus, a 5% rhenium/zirconium oxide catalyst (catalyst such that the amount of rhenium included in the catalyst to the total mass of the catalyst was 5% by mass) was collected. The specific surface area of the catalyst was 91 $m^2/g$. The average valence of Re included in the catalyst was 4.4, that is, "4". The zirconium oxide included in the catalyst was monoclinic. That is, the ratio of the peak intensity of tetragonal crystal phase (2θ peak at about 30°) to the peak intensity of monoclinic phase (2θ peak at about 28.2°) of the zirconium oxide was 0. The mass ratio of the tetragonal zirconium oxide to the monoclinic zirconium oxide (hereinafter, this ratio is referred to as "tetragonal/monoclinic ratio") was 0.

Into a 70-mL high-pressure reactor, 100 mg of the catalyst prepared by the above method, 500 mg of sebacic acid, 2 g of water, and a stirrer chip were charged. After the reactor had been purged with nitrogen, a hydrogen gas (7 MPaG) was introduced into the reactor at room temperature. Subsequently, a hydrogenation reaction was conducted at 220° C. for 7.5 hours. The reaction pressure at 220° C. was 13 MPaG.

After the reaction had been terminated, the temperature was reduced to room temperature and the pressure was then reduced. An analysis of the reaction liquid by gas chromatography confirmed that the molar yields of 1,10-decanediol and 10-hydroxydecanoic acid in the reaction were 49.8% and 6.9%, respectively, and the molar ratio of the by-products (1-nonanol, 1-decanol, 1-nonanoic acid, and 1-decanoic acid) to the target components (1,10-decanediol and 10-hydroxydecanoic acid) was 0.12. The catalytic activity index defined below (hereinafter, referred to as "catalytic activity index I") was 53.2.

<Catalytic Activity Index I>

"Yield of 1,10-decanediol"+"½ of Yield of 10-hydroxydecanoic acid (reaction intermediate of 1,10-decanediol)"

Example I-1-B

The catalyst prepared in Example I-1-A was treated in air at 40° C. for 1 hour to prepare an air-stabilized, 5% rhenium/zirconium oxide catalyst. The specific surface area of the catalyst was 91 $m^2/g$. The zirconium oxide included in the catalyst was monoclinic. That is, the ratio of the peak intensity of tetragonal crystal phase (2θ peak at about 30°) to the peak intensity of monoclinic phase (2θ peak at about) 28.2° of the zirconium oxide was 0. The tetragonal/monoclinic ratio was 0.

The hydrogenation reaction was conducted as in Example I-1-A with the catalyst. The molar yields of 1,10-decanediol and 10-hydroxydecanoic acid in the reaction were 42.1% and 11.6%, respectively. The molar ratio of the by-products (1-nonanol, 1-decanol, 1-nonanoic acid, and 1-decanoic acid) to the target components (1,10-decanediol and 10-hydroxydecanoic acid) was 0.13. The catalytic activity index I was 47.9.

Reference Example I-1-A

Zirconium hydroxide $Zr(OH)_4 \cdot nH_2O$ (produced by Daiichi Kigenso Kagaku Kogyo Co., Ltd.) was charged into a vertical calcination tube. While air was passed through the tube, a calcination treatment was performed at 500° C. for 4 hours to prepare zirconium oxide that included monoclinic and tetragonal phases at a ratio of 37:63 and had a specific surface area of 40 m$^2$/g.

A 5% rhenium/zirconium oxide catalyst was prepared as in Example I-1-A, except that the zirconium oxide prepared above was used as a carrier. The specific surface area of the catalyst was 43 m$^2$/g. The ratio of the peak intensity of tetragonal crystal phase (2θ peak at about 30°) to the peak intensity of monoclinic phase (2θ peak at about 28.2°) of the zirconium oxide included in the catalyst was 1.7. The tetragonal/monoclinic ratio was 1.1.

The hydrogenation reaction was conducted as in Example I-1-A with the catalyst. The molar yields of 1,10-decanediol and 10-hydroxydecanoic acid in the reaction were 10.5% and 40.2%, respectively. The molar ratio of the by-products (1-nonanol, 1-decanol, 1-nonanoic acid, and 1-decanoic acid) to the target components (1,10-decanediol and 10-hydroxydecanoic acid) was 0.03. The catalytic activity index I was 30.6.

Reference Example I-1-B

The catalyst prepared in Reference example I-1-A was treated in air at 40° C. for 1 hour to prepare an air-stabilized, 5% rhenium/zirconium oxide catalyst. The specific surface area of the catalyst was 43 m$^2$/g. The ratio of the peak intensity of tetragonal crystal phase (2θ peak at about 30°) to the peak intensity of monoclinic phase (2θ peak at about 28.2°) of the zirconium oxide included in the catalyst was 1.7. The tetragonal/monoclinic ratio was 1.1.

The hydrogenation reaction was conducted as in Example I-1-A with the catalyst. The molar yields of 1,10-decanediol and 10-hydroxydecanoic acid in the reaction were 7.4% and 36.5%, respectively. The molar ratio of the by-products (1-nonanol, 1-decanol, 1-nonanoic acid, and 1-decanoic acid) to the target components (1,10-decanediol and 10-hydroxydecanoic acid) was 0.03. The catalytic activity index I was 25.7.

Example I-2-A

A 5% rhenium-5% germanium/zirconium oxide catalyst was prepared as in the catalyst preparation method used in Example I-1-A, except that ammonium perrhenate and tetraethoxygermanium(IV) were used as metal raw materials. The specific surface area of the catalyst was 96 m$^2$/g. The average valence of Re included in the catalyst was 0. The zirconium oxide included in the catalyst was monoclinic. That is, the ratio of the peak intensity of tetragonal crystal phase (2θ peak at about 30°) to the peak intensity of monoclinic phase (2θ peak at about 28.2°) of the zirconium oxide was 0. The tetragonal/monoclinic ratio was 0.

The hydrogenation reaction was conducted as in Example I-1-A with the catalyst. The molar yields of 1,10-decanediol and 10-hydroxydecanoic acid in the reaction were 36.3% and 19.6%, respectively. The molar ratio of the by-products (1-nonanol, 1-decanol, 1-nonanoic acid, and 1-decanoic acid) to the target components (1,10-decanediol and 10-hydroxydecanoic acid) was 0.005. The catalytic activity index I was 46.1.

Example I-2-B

The catalyst prepared in Example I-2-A was treated in air at 40° C. for 1 hour to prepare an air-stabilized, 5% rhenium-5% germanium/zirconium oxide catalyst. The specific surface area of the catalyst was 96 m$^2$/g. The average valence of Re included in the catalyst was 0.4. The zirconium oxide included in the catalyst was monoclinic. That is, the ratio of the peak intensity of tetragonal crystal phase (2θ peak at about 30°) to the peak intensity of monoclinic phase (2θ peak at about 28.2°) of the zirconium oxide was 0. The tetragonal/monoclinic ratio was 0.

The hydrogenation reaction was conducted as in Example I-1-A with the catalyst. The molar yields of 1,10-decanediol and 10-hydroxydecanoic acid in the reaction were 23.4% and 44.6%, respectively. The molar ratio of the by-products (1-nonanol, 1-decanol, 1-nonanoic acid, and 1-decanoic acid) to the target components (1,10-decanediol and 10-hydroxydecanoic acid) was 0.006. The catalytic activity index I was 45.7.

Comparative Example I-1-A

A 5% rhenium/titanium oxide catalyst was prepared as in the catalyst preparation method used in Example I-1-A, except that titanium oxide (reference catalyst of the Catalysis Society of Japan, JRC-TIO-14, produced by Ishihara Sangyo Kaisha, Ltd.) having a specific surface area of 308 m$^2$/g was used as a carrier. The specific surface area of the catalyst was 66 m$^2$/g. The average valence of Re included in the catalyst was 4.6. The catalyst did not include zirconium oxide.

The hydrogenation reaction was conducted as in Example I-1-A with the catalyst. The molar yields of 1,10-decanediol and 10-hydroxydecanoic acid in the reaction were 94.4% and 0.5%, respectively. The molar ratio of the by-products (1-nonanol, 1-decanol, 1-nonanoic acid, and 1-decanoic acid) to the target components (1,10-decanediol and 10-hydroxydecanoic acid) was 0.02. The catalytic activity index I was 94.7.

Comparative Example I-1-B

A 5% rhenium/titanium oxide catalyst was prepared as in the catalyst preparation method used in Comparative example I-1-A, except that, subsequent to the reduction treatment, cooling was performed, purging was then performed with argon, and subsequently a surface stabilization treatment was performed by passing a 6-volume % oxygen/nitrogen gas at 25° C. for 1 hour. The catalyst did not include zirconium oxide.

The hydrogenation reaction was conducted as in Example I-1-A with the catalyst. The molar yields of 1,10-decanediol and 10-hydroxydecanoic acid in the reaction were 0.1% and 20.0%, respectively. The molar ratio of the by-products (1-nonanol, 1-decanol, 1-nonanoic acid, and 1-decanoic acid) to the target components (1,10-decanediol and 10-hydroxydecanoic acid) was 0.06. The catalytic activity index I was 10.1.

Reference Example I-2-A

A 5% rhenium/zirconium oxide catalyst was prepared as in the catalyst preparation method used in Example I-1-A, except that, tetragonal zirconium oxide (produced by Saint-Gobain, purity: 94%) having a specific surface area of 168 m$^2$/g was used as a carrier. The specific surface area of the catalyst was 155 m$^2$/g. The zirconium oxide included in the catalyst was tetragonal. That is, the ratio of the peak intensity of tetragonal crystal phase (2θ peak at about 30°) to the peak intensity of monoclinic phase (2θ peak at about) 28.2° of the zirconium oxide included in the catalyst was ∞, and the tetragonal/monoclinic ratio was ∞.

The hydrogenation reaction was conducted as in Example I-1-A with the catalyst. The molar yields of 1,10-decanediol and 10-hydroxydecanoic acid in the reaction were 6.1% and 33.7%, respectively. The molar ratio of the by-products (1-nonanol, 1-decanol, 1-nonanoic acid, and 1-decanoic acid) to the target components (1,10-decanediol and 10-hydroxydecanoic acid) was 0.02. The catalytic activity index I was 22.9.

Reference Example I-2-B

The catalyst prepared in Reference example I-2-A was treated in air at 40° C. for 1 hour to prepare an air-stabilized, 5% rhenium/zirconium oxide catalyst. The specific surface area of the catalyst was 155 $m^2/g$. The zirconium oxide included in the catalyst was tetragonal. That is, the ratio of the peak intensity of tetragonal crystal phase (2θ peak at about 30°) to the peak intensity of monoclinic phase (2θ peak at about 28.2°) of the zirconium oxide included in the catalyst was ∞, and the tetragonal/monoclinic ratio was ∞.

The hydrogenation reaction was conducted as in Example I-1-A with the catalyst. The molar yields of 1,10-decanediol and 10-hydroxydecanoic acid in the reaction were 7.7% and 38.0%, respectively. The molar ratio of the by-products (1-nonanol, 1-decanol, 1-nonanoic acid, and 1-decanoic acid) to the target components (1,10-decanediol and 10-hydroxydecanoic acid) was 0.07. The catalytic activity index I was 26.7.

Reference Example I-3

A 5% rhenium-5% germanium-0.5% ruthenium/zirconium oxide catalyst was prepared as in the catalyst preparation method used in Example I-1-A, except that ammonium perrhenate, tetraethoxygermanium(IV), and ruthenium(III) chloride were used as metal raw materials. The specific surface area of the catalyst was 90 $m^2/g$. The zirconium oxide included in the catalyst was monoclinic. That is, the ratio of the peak intensity of tetragonal crystal phase (2θ peak at about 30°) to the peak intensity of monoclinic phase (2θ peak at about 28.2°) of the zirconium oxide was 0. The tetragonal/monoclinic ratio was 0.

The hydrogenation reaction was conducted as in Example I-1-A with the catalyst. The molar yields of 1,10-decanediol and 10-hydroxydecanoic acid in the reaction were 31.0% and 39.3%, respectively. The molar ratio of the by-products (1-nonanol, 1-decanol, 1-nonanoic acid, and 1-decanoic acid) to the target components (1,10-decanediol and 10-hydroxydecanoic acid) was 0.01. The catalytic activity index I was 50.6.

Reference Example I-4

A 5% rhenium-5% germanium-5% ruthenium/zirconium oxide catalyst was prepared as in the catalyst preparation method used in Example I-1-A, except that ammonium perrhenate, tetraethoxygermanium(IV), and ruthenium(III) chloride were used as metal raw materials. The specific surface area of the catalyst was 95 $m^2/g$. The zirconium oxide included in the catalyst was monoclinic. That is, the ratio of the peak intensity of tetragonal crystal phase (2θ peak at about 30°) to the peak intensity of monoclinic phase (2θ peak at about) 28.2° of the zirconium oxide was 0. The tetragonal/monoclinic ratio was 0.

The hydrogenation reaction was conducted as in Example I-1-A with the catalyst. The molar yields of 1,10-decanediol and 10-hydroxydecanoic acid in the reaction were 11.4% and 37.3%, respectively. The molar ratio of the by-products (1-nonanol, 1-decanol, 1-nonanoic acid, and 1-decanoic acid) to the target components (1,10-decanediol and 10-hydroxydecanoic acid) was 0.02. The catalytic activity index I was 30.0.

Table 1 summarizes the results.

TABLE 1

| | Catalyst | | Average valence of Re | Specific surface area of catalyst ($m^2/g$) | ZrO$_2$ content in carrier (mass %) | Tetragonal/monoclinic ratio | Yield of 1,10-decanediol (mol%) | Yield of 10-hydroxydecanoic acid (mol%) | Molar ratio of by-products/target components | Catalytic activity index I |
|---|---|---|---|---|---|---|---|---|---|---|
| Example I-1-A | 5%Re/ZrO$_2$ | After reduction treatment | 4.4 | 91 | 100 | 0 | 49.8 | 6.9 | 0.12 | 53.2 |
| Example I-1-B | | After oxidative stabilization | — | | | | 42.1 | 11.6 | 0.13 | 47.9 |
| Reference example I-1-A | 5%Re/ZrO$_2$ | After reduction treatment | — | 43 | 100 | 1.1 | 10.5 | 40.2 | 0.03 | 30.6 |
| Reference example I-1-B | | After oxidative stabilization | | | | | 7.4 | 36.5 | 0.03 | 25.7 |
| Example I-2-A | 5%Re-5%Ge/ZrO$_2$ | After reduction treatment | 0 | 96 | 100 | 0 | 36.3 | 19.6 | 0.005 | 46.1 |
| Example I-2-B | | After oxidative stabilization | | | | | 23.4 | 44.6 | 0.006 | 45.7 |

TABLE 1-continued

| | Catalyst | | Average valence of Re | Specific surface area of catalyst (m²/g) | ZrO₂ content in carrier (mass %) | Tetragonal/monoclinic ratio | Reaction results | | | Catalytic activity index I |
|---|---|---|---|---|---|---|---|---|---|---|
| | | | | | | | Yield of 1,10-decanediol (mol%) | Yield of 10-hydroxydecanoic acid (mol%) | Molar ratio of by-products/target components | |
| Comparative example I-1-A | 5%Re/TiO₂ | After reduction treatment | 4.6 | 66 | 0 | — | 94.4 | 0.5 | 0.02 | 94.7 |
| Comparative example I-1-B | | After oxidative stabilization | | | | | 0.1 | 20.0 | 0.06 | 10.1 |
| Reference example I-2-A | 5%Re/ZrO₂ | After reduction treatment | — | 155 | 94 | ∞ | 6.1 | 33.7 | 0.02 | 22.9 |
| Reference example I-2-B | | After oxidative stabilization | | | | | 7.7 | 38.0 | 0.07 | 26.7 |
| Reference example 1-3 | 5%Re-5%Ge-0.5%Ru/ZrO₂ | After reduction treatment | — | 90 | 100 | 0 | 31.0 | 39.3 | 0.01 | 50.6 |
| Reference example 1-4 | 5%Re-5%Ge-5%Ru/ZrO₂ | After reduction treatment | — | 95 | 100 | 0 | 11.4 | 37.3 | 0.02 | 30.0 |

The results obtained in Examples and Comparative examples confirm the following facts.

A comparison between Examples I-1-A and I-1-B and Comparative examples I-1-A and I-1-B confirms that reductions in the activities of zirconium oxide carrier catalysts which are caused due to oxidation stabilization are markedly small compared with titanium oxide carrier catalysts known in the related art. This proves that the rhenium/zirconium oxide catalyst may be advantageously used as an industrial catalyst that can be handled in air.

The results of the reactions conducted in Examples and Comparative examples confirm the following facts.

Among rhenium/zirconium oxide catalysts, the higher the content of monoclinic zirconium oxide, the higher the catalytic activity per unit area. In addition, adding any of the elements of Groups 13 to 15 in the third and higher periods of the periodic table to the rhenium/zirconium oxide catalyst as a supported metal may markedly enhance the reaction selectivity.

The above results confirm that, the higher the content of monoclinic zirconium oxide in the rhenium-supporting catalyst used, the higher the catalytic activity of the catalyst in the hydrogenation reaction of a carboxylic acid and the higher the ease of handling of the catalyst which allows the catalyst to be handled in air.

The catalyst having the above-described properties is markedly valuable as an industrial catalyst used for synthesizing an alcohol directly from a carbonyl compound.

Example II-1

Ammonium perrhenate was dissolved in water. Monoclinic zirconium oxide having a specific surface area of 97 m²/g (produced by Saint-Gobain) used as a carrier was added to the resulting solution. The resulting mixture was stirred at room temperature for 1 hour. Subsequently, water was removed using an evaporator. Then, drying was performed at 100° C. for 3 hours. The resulting material was charged into a vertical calcination tube. While air was passed through the tube, a calcination treatment was performed at 500° C. for 3 hours. The resulting solid was charged into another vertical calcination tube. While a hydrogen gas was passed through the tube, a reduction treatment was performed at 500° C. for 30 minutes. Subsequently, the temperature was reduced to 30° C. Then, purging was performed with an argon gas. Thus, a 5% rhenium/zirconium oxide catalyst (catalyst such that the amount of rhenium included in the catalyst to the total mass of the catalyst was 5% by mass) was collected. The specific surface area of the catalyst was 91 m²/g. The zirconium oxide included in the catalyst was monoclinic. The average valence of Re included in the catalyst was 4.4, that is, "4".

Into a 70-mL high-pressure reactor, 100 mg of the catalyst prepared by the above method, 500 mg of sebacic acid, 2 g of water, and a stirrer chip were charged. After the reactor had been purged with nitrogen, a hydrogen gas (7 MPaG) was introduced into the reactor at room temperature. Subsequently, a hydrogenation reaction was conducted at 220° C. for 3 hours. The reaction pressure at 220° C. was 13 MPaG.

After the reaction had been terminated, the temperature was reduced to room temperature and the pressure was then reduced. An analysis of the reaction liquid by gas chromatography confirmed that the molar yields of 1,10-decanediol and 10-hydroxydecanoic acid in the reaction were 8.2% and 41.4%, respectively, and the molar ratio of the by-products (1-nonanol, 1-decanol, 1-nonanoic acid, and 1-decanoic acid) to the target components (1,10-decanediol and 10-hydroxydecanoic acid) was 0.073. The catalytic activity index per amount of rhenium supported which is defined below (hereinafter, referred to as "catalytic activity index II") was 5.8.

<Catalytic Activity Index II Per Amount of Rhenium Supported>

("Yield of 1,10-decanediol"+"½ of Yield of 10-hydroxydecanoic acid (reaction intermediate of 1,10-decanediol)")/Amount of rhenium supported on catalyst (mass %)

Example II-2

A 5% rhenium-1% germanium/zirconium oxide catalyst was prepared as in the catalyst preparation method used in Example II-1, except that ammonium perrhenate and tetraethoxygermanium(IV) were used as metal raw materials. The zirconium oxide included in the catalyst was monoclinic. The average valence of Re included in the catalyst was 2.7, that is, "3".

The hydrogenation reaction was conducted as in Example II-1 with the catalyst. The molar yields of 1,10-decanediol and 10-hydroxydecanoic acid in the reaction were 13.0% and 55.9%, respectively. The molar ratio of the by-products (1-nonanol, 1-decanol, 1-nonanoic acid, and 1-decanoic acid) to the target components (1,10-decanediol and 10-hydroxydecanoic acid) was 0.009. The catalytic activity index II was 8.2.

Example II-3

A 5% rhenium-3% germanium/zirconium oxide catalyst was prepared as in the catalyst preparation method used in Example II-2, except that the weights of the ammonium perrhenate and tetraethoxygermanium(IV) used as metal raw materials were changed. The zirconium oxide included in the catalyst was monoclinic. The average valence of Re included in the catalyst was 0.5, that is, "1".

The hydrogenation reaction was conducted as in Example II-1 with the catalyst. The molar yields of 1,10-decanediol and 10-hydroxydecanoic acid in the reaction were 30.4% and 47.6%, respectively. The molar ratio of the by-products (1-nonanol, 1-decanol, 1-nonanoic acid, and 1-decanoic acid) to the target components (1,10-decanediol and 10-hydroxydecanoic acid) was 0.001. The catalytic activity index II was 10.9.

Example II-4

A 5% rhenium-5% germanium/zirconium oxide catalyst was prepared as in the catalyst preparation method used in Example II-2, except that the weights of the ammonium perrhenate and tetraethoxygermanium(IV) used as metal raw materials were changed. The specific surface area of the catalyst was 96 m$^2$/g. The zirconium oxide included in the catalyst was monoclinic. The average valence of rhenium was 0.

The hydrogenation reaction was conducted as in Example II-1 with the catalyst. The molar yields of 1,10-decanediol and 10-hydroxydecanoic acid in the reaction were 15.6% and 66.2%, respectively. The molar ratio of the by-products (1-nonanol, 1-decanol, 1-nonanoic acid, and 1-decanoic acid) to the target components (1,10-decanediol and 10-hydroxydecanoic acid) was 0.001. The catalytic activity index II was 9.7.

Example II-5

A 10% rhenium/zirconium oxide catalyst was prepared as in the catalyst preparation method used in Example II-1, except that the weight of the ammonium perrhenate used as a metal raw material was changed. The zirconium oxide included in the catalyst was monoclinic. The average valence of Re included in the catalyst was 2.0, that is, "2".

The hydrogenation reaction was conducted as in Example II-1 with the catalyst. The molar yields of 1,10-decanediol and 10-hydroxydecanoic acid in the reaction were 51.7% and 8.0%, respectively. The molar ratio of the by-products (1-nonanol, 1-decanol, 1-nonanoic acid, and 1-decanoic acid) to the target components (1,10-decanediol and 10-hydroxydecanoic acid) was 0.038. The catalytic activity index II was 5.6.

Example II-6

A 10% rhenium-2% germanium/zirconium oxide catalyst was prepared as in the catalyst preparation method used in Example II-2, except that the weights of the ammonium perrhenate and tetraethoxygermanium(IV) used as metal raw materials were changed. The zirconium oxide included in the catalyst was monoclinic. The average valence of Re included in the catalyst was 1.5, that is, "2".

The hydrogenation reaction was conducted as in Example II-1 with the catalyst. The molar yields of 1,10-decanediol and 10-hydroxydecanoic acid in the reaction were 49.9% and 18.4%, respectively. The molar ratio of the by-products (1-nonanol, 1-decanol, 1-nonanoic acid, and 1-decanoic acid) to the target components (1,10-decanediol and 10-hydroxydecanoic acid) was 0.010. The catalytic activity index II was 5.9.

Example II-7

A 15% rhenium/zirconium oxide catalyst was prepared as in the catalyst preparation method used in Example II-1, except that the weight of the ammonium perrhenate used as a metal raw material was changed. The zirconium oxide included in the catalyst was monoclinic. The average valence of Re included in the catalyst was 4.4, that is, "4".

The hydrogenation reaction was conducted as in Example II-1 with the catalyst. The molar yields of 1,10-decanediol and 10-hydroxydecanoic acid in the reaction were 30.3% and 34.6%, respectively. The molar ratio of the by-products (1-nonanol, 1-decanol, 1-nonanoic acid, and 1-decanoic acid) to the target components (1,10-decanediol and 10-hydroxydecanoic acid) was 0.032. The catalytic activity index II was 3.2.

Comparative Example II-1

Ammonium perrhenate was dissolved in water. Monoclinic zirconium oxide having a specific surface area of 97 m$^2$/g (produced by Saint-Gobain) used as a carrier was added to the resulting solution. The resulting mixture was stirred at room temperature for 1 hour. Subsequently, water was removed using an evaporator. Then, drying was performed at 100° C. for 3 hours. The resulting material was charged into a vertical calcination tube. While air was passed through the tube, a calcination treatment was performed at 500° C. for 3 hours. Hereby, an air-calcined, 5% rhenium/zirconium oxide catalyst was prepared. The zirconium oxide included in the catalyst was monoclinic. The average valence of Re included in the catalyst was 7.

The hydrogenation reaction was conducted as in Example II-1 with the catalyst. The molar yields of 1,10-decanediol and 10-hydroxydecanoic acid in the reaction were 1.1% and 5.6%, respectively. The molar ratio of the by-products (1-nonanol, 1-decanol, 1-nonanoic acid, and 1-decanoic acid) to the target components (1,10-decanediol and 10-hydroxydecanoic acid) was 0.086. The catalytic activity index II was 0.8.

Comparative Example II-2

Ammonium perrhenate was dissolved in water. Tetragonal zirconium oxide having a specific surface area of 168 m$^2$/g (produced by Saint-Gobain, purity: 94%) used as a carrier was added to the resulting solution. The resulting mixture was stirred at room temperature for 1 hour. Subsequently, water was removed using an evaporator. Then, drying was performed at 100° C. for 3 hours. The resulting material was charged into a vertical calcination tube. While air was passed through the tube, a calcination treatment was performed at 500° C. for 3 hours. Hereby, an air-calcined, 5% rhenium/zirconium oxide catalyst was prepared. The zirconium oxide included in the catalyst was tetragonal. The average valence of Re included in the catalyst was 7.

The hydrogenation reaction was conducted as in Example II-1 with the catalyst. The molar yields of 1,10-decanediol and 10-hydroxydecanoic acid in the reaction were 0.9% and 5.3%, respectively. The molar ratio of the by-products (1-nonanol, 1-decanol, 1-nonanoic acid, and 1-decanoic acid) to the target components (1,10-decanediol and 10-hydroxydecanoic acid) was 0.106. The catalytic activity index II was 0.7.

Table 2 summarizes the results.

increase the total amount of 1,10-decanediol and 10-hydroxydecanoic acid produced in the hydrogenation reaction of a carboxylic acid per amount (mass %) of the rhenium supported. Note that, the total amount of 1,10-decanediol and 10-hydroxydecanoic acid produced is used as a measure of catalytic activity because 10-hydroxydecanoic acid is considered a reaction intermediate of the 1,10-decanediol product and can be derived into 1,10-decanediol when the reaction time is further prolonged. The remarkable increase in hydrogenation catalytic activity may contribute to reductions in the costs of production of alcohols.

The above results prove that a catalyst that includes a metal component including rhenium having an average valence of 4 or less and a carrier that supports the metal component and includes zirconium oxide may produce excellent catalytic activity in the hydrogenation reaction of a carboxylic acid.

The catalyst having the above-described properties is markedly valuable as an industrial catalyst used for synthesizing an alcohol directly from a carbonyl compound.

Although the present invention has been described in detail with reference to particular embodiments, it is apparent to a person skilled in the art that various modifications can be made therein without departing from the spirit and scope of the present invention.

TABLE 21

| Catalyst | | Average valence of Re | Monoclinic ZrO$_2$ content in carrier (mass %) | Reaction results | | | Catalytic activity index II |
|---|---|---|---|---|---|---|---|
| | | | | Yield of 1,10-decanediol (mol %) | Yield of 10-hydroxydecanoic acid (mol %) | Molar ratio of by-products/target components | |
| Example II-1 | 5%Re/ZrO$_2$ | 4.4 | 100 | 8.2 | 41.4 | 0.073 | 5.8 |
| Example II-2 | 5%Re-1%Ge/ZrO$_2$ | 2.7 | 100 | 13.0 | 55.9 | 0.009 | 8.2 |
| Example II-3 | 5%Re-3%Ge/ZrO$_2$ | 0.5 | 100 | 30.4 | 47.6 | 0.001 | 10.9 |
| Example II-4 | 5%Re-5%Ge/ZrO$_2$ | 0 | 100 | 15.6 | 66.2 | 0.001 | 9.7 |
| Example II-5 | 10%Re/ZrO$_2$ | 2.0 | 100 | 51.7 | 8.0 | 0.038 | 5.6 |
| Example II-6 | 10%Re-2%Ge/ZrO$_2$ | 1.5 | 100 | 49.9 | 18.4 | 0.010 | 5.9 |
| Example II-7 | 15%Re/ZrO$_2$ | 4.4 | 100 | 30.3 | 34.6 | 0.032 | 3.2 |
| Comparative example II-1 | 5%Re/ZrO$_2$ | 7 | 100 | 1.1 | 5.6 | 0.086 | 0.8 |
| Comparative example II-2 | 5%Re/ZrO$_2$ | 7 | 0 | 0.9 | 5.3 | 0.106 | 0.7 |

The results obtained in Examples and Comparative examples above confirm the following facts.

A comparison between Examples II-1 to II-7 and Comparative example II-1 confirms that the use of a catalyst that includes a metal component including rhenium having an average valence of 4 or less and a carrier that supports the metal component and includes zirconium oxide may The present application is based on Japanese Patent Application No. 2018-137792 filed on Jul. 23, 2018, which is incorporated herein by reference in its entirety.

INDUSTRIAL APPLICABILITY

The catalyst is industrially useful as a catalyst for directly synthesizing an alcohol from a carbonyl compound. The catalyst enables an intended alcohol to be produced with high activity and high selectivity. The catalyst is so easy to handle that it can be handled in air and may reduce increases in the costs of purification of the product and the costs of production of the catalyst. Therefore, the catalyst is industrially highly valuable.

The invention claimed is:

1. An alcohol production method in which an alcohol is produced from a carbonyl compound, the method comprising producing an alcohol by using a catalyst, the catalyst including a metal component including rhenium having an average valence of 4 or less, wherein a content of a metal of groups 8 to 10 of the periodic table except iron and nickel included in the catalyst is less than 0.2 in terms of atomic mass ratio to the rhenium atoms, and a carrier supporting the metal component, the carrier including zirconium oxide.

2. The alcohol production method according to claim 1, wherein the carrier includes at least monoclinic and/or tetragonal zirconium oxide.

3. The alcohol production method according to claim 2, wherein the carrier includes at least monoclinic zirconium oxide.

4. The alcohol production method according to claim 3, wherein the carrier further includes tetragonal zirconium oxide, and wherein a mass ratio of the tetragonal zirconium oxide to the monoclinic zirconium oxide is 3 or less.

5. The alcohol production method according to claim 1, wherein the carrier is zirconium oxide.

6. The alcohol production method according to claim 1, wherein the carrier has a specific surface area of 30 m2/g or more.

7. The alcohol production method according to claim 1, wherein the metal component includes one or more elements selected from elements of Groups 13 to 15 in the third and higher periods of the periodic table, the one or more elements being used as a second component.

8. The alcohol production method according to claim 7, wherein a mass ratio of the elements used as the second component to the rhenium element included in the metal component is 0.1 or more and 3 or less.

9. The alcohol production method according to claim 7, wherein the metal component includes germanium that is an element used as the second component.

10. The alcohol production method according to claim 1, wherein the carbonyl compound is one or more compounds selected from carboxylic acids, carboxylic acid esters, carboxylic anhydrides, and aldehydes.

11. The alcohol production method according to claim 1, wherein alcohol is produced in the presence of hydrogen gas.

12. The alcohol production method according to claim 1, wherein an action in the method is a reduction reaction in a liquid phase using a solvent.

13. The alcohol production method according to claim 12, wherein the solvent is water.

14. The alcohol production method according to claim 12, wherein the solvent is an alcohol.

15. The alcohol production method according to claim 12, wherein the solvent is an ether.

16. The alcohol production method according to claim 12, wherein the solvent is a hydrocarbon.

17. The alcohol production method according to claim 1, wherein the reaction temperature is 100 to 300° C. and the reaction pressure is 1 to 30 MPa G.

18. The alcohol production method according to claim 1, wherein a carbon-oxygen double bond in the carbonyl compound is converted to obtain a corresponding alcohol.

* * * * *